(12) United States Patent
Hirata et al.

(10) Patent No.: US 10,300,197 B2
(45) Date of Patent: May 28, 2019

(54) DROPPING RATE MEASURING DEVICE, DROPPING RATE CONTROLLER, DRIP INFUSION DEVICE, AND LIQUID DROPLET VOLUME MEASURING DEVICE

(71) Applicant: Murata Manufacturing Co., Ltd., Kyoto (JP)

(72) Inventors: Atsuhiko Hirata, Kyoto (JP); Nobuhiro Kondo, Kyoto (JP); Yuzo Higashiyama, Kyoto (JP); Yoshitaka Hane, Kyoto (JP); Yoshihide Amagai, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 23 days.

(21) Appl. No.: 15/647,733

(22) Filed: Jul. 12, 2017

(65) Prior Publication Data

US 2017/0304535 A1 Oct. 26, 2017

Related U.S. Application Data

(63) Continuation of application No. PCT/JP2016/050716, filed on Jan. 12, 2016.

(30) Foreign Application Priority Data

Jan. 13, 2015 (JP) .................................. 2015-003987
May 27, 2015 (JP) .................................. 2015-107359

(51) Int. Cl.
*A61M 5/168* (2006.01)
*A61M 5/14* (2006.01)
*A61M 5/142* (2006.01)

(52) U.S. Cl.
CPC ............ *A61M 5/1689* (2013.01); *A61M 5/14* (2013.01); *A61M 5/142* (2013.01);
(Continued)

(58) Field of Classification Search
CPC ............. A61M 5/1689; A61M 5/1411; A61M 5/16877; A61M 5/16804; A61M 5/16886;
(Continued)

(56) References Cited

U.S. PATENT DOCUMENTS

| 6,159,186 A * | 12/2000 | Wickham ............ A61M 5/1689 604/251 |
| 2012/0095433 A1* | 4/2012 | Hungerford ........ A61M 5/1689 604/500 |
| 2013/0188040 A1* | 7/2013 | Kamen ............... G06F 19/3418 348/135 |

FOREIGN PATENT DOCUMENTS

| JP | H01-197613 | 8/1989 |
| JP | H09-192217 A | 7/1997 |

(Continued)

OTHER PUBLICATIONS

International Search Report issued in Application No. PCT/JP2016/050716 dated Apr. 5, 2016.
(Continued)

*Primary Examiner* — Nathan R Price
*Assistant Examiner* — Anh Bui
(74) *Attorney, Agent, or Firm* — Pearne & Gordon LLP

(57) ABSTRACT

A dropping rate measuring device for measuring a flow rate of liquid droplets which grow on a lower end of a nozzle and intermittently drop from the lower end of the nozzle includes an imaging unit that images a growing liquid droplet which is growing on the lower end of the nozzle at a plurality of time points and acquires a plurality of pieces of image data of the growing liquid droplet, and a data processor that calculates the flow rate by analyzing the plurality of pieces of image data acquired by the imaging unit.

18 Claims, 25 Drawing Sheets

(52) U.S. Cl.
CPC .......... *A61M 5/1411* (2013.01); *A61M 5/168* (2013.01); *A61M 5/1684* (2013.01); *A61M 5/16804* (2013.01); *A61M 5/16877* (2013.01); *A61M 5/16886* (2013.01); *A61M 2205/18* (2013.01); *A61M 2205/3306* (2013.01); *A61M 2205/3379* (2013.01); *A61M 2205/50* (2013.01)

(58) Field of Classification Search
CPC .......... A61M 5/168; A61M 2205/3306; A61M 2205/3379
See application file for complete search history.

(56) References Cited

FOREIGN PATENT DOCUMENTS

| | | | |
|---|---|---|---|
| JP | 2005-006875 A | | 1/2005 |
| JP | 2005006875 A | * | 1/2005 |
| JP | 2012-125450 A | | 7/2012 |
| JP | 5131894 B2 | | 1/2013 |
| JP | 5583939 B2 | | 9/2014 |

OTHER PUBLICATIONS

Written Opinion issued in Application No. PCT/JP2016/050716 dated Apr. 5, 2016.

* cited by examiner

FIG.3
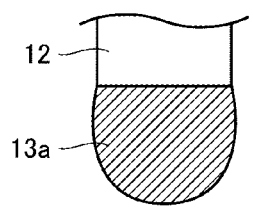
FIG.4
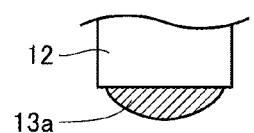
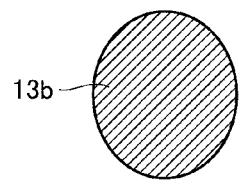

VOLUME OF ONE DROPLET

NUMBER OF TIMES OF DROPPING

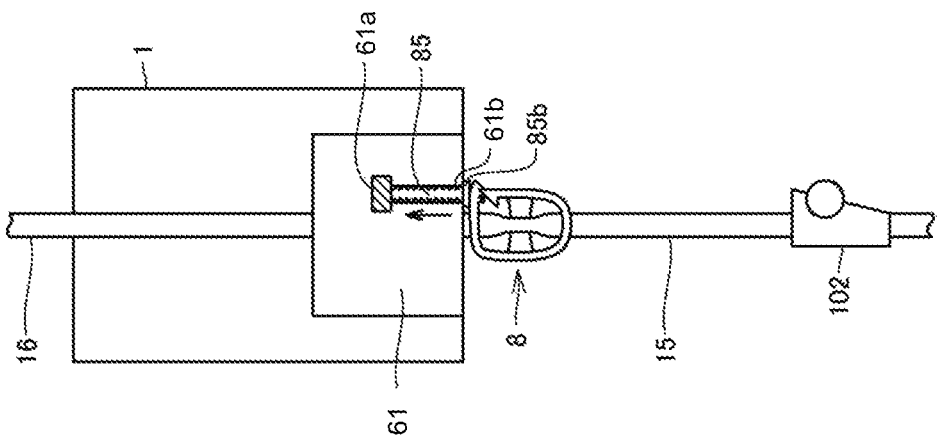
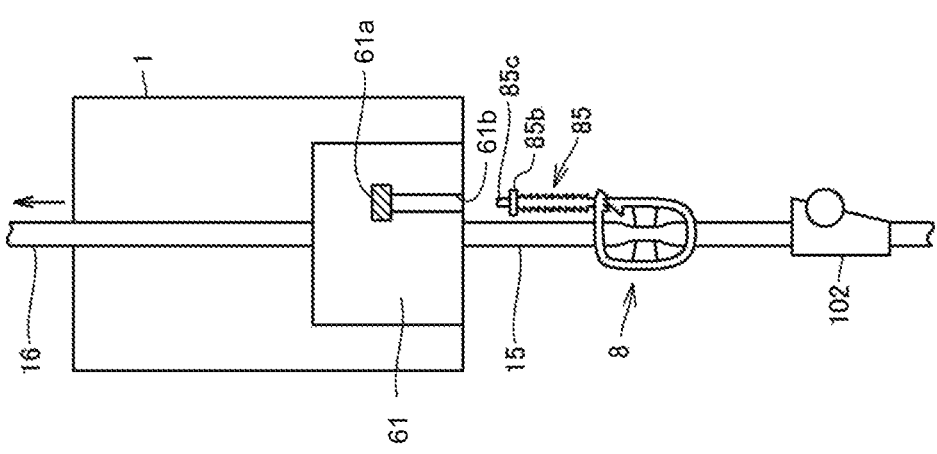
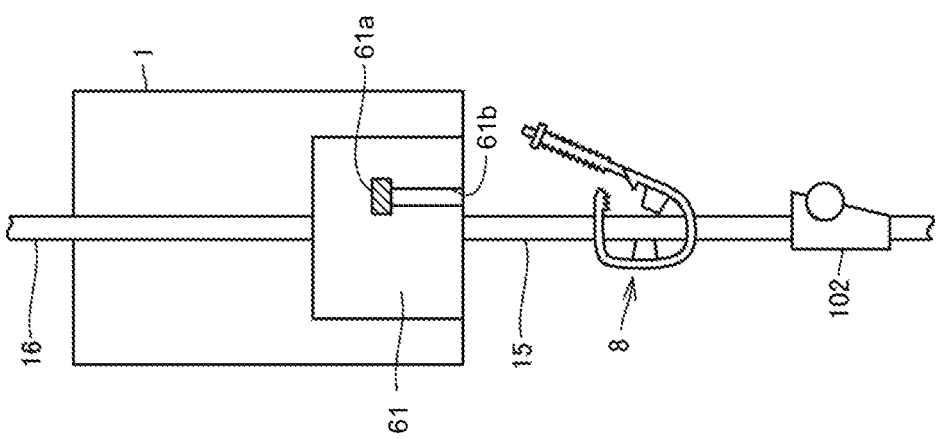

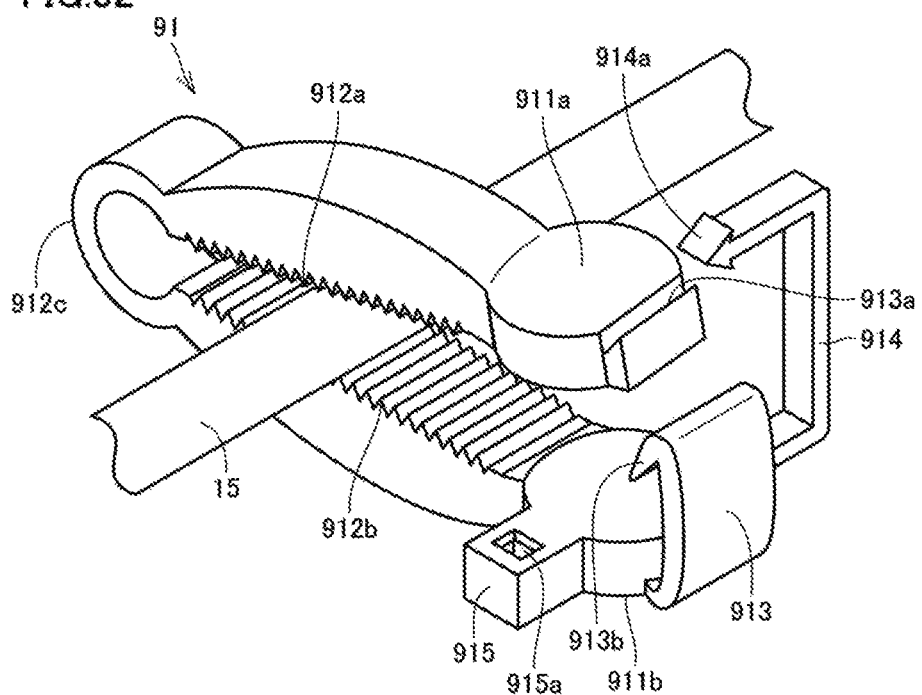

10,300,197 B2

DROPPING RATE MEASURING DEVICE, DROPPING RATE CONTROLLER, DRIP INFUSION DEVICE, AND LIQUID DROPLET VOLUME MEASURING DEVICE

This is a continuation of International Application No. PCT/JP2016/050716 filed on Jan. 12, 2016 which claims priority from Japanese Patent Application Nos. 2015-107359 filed on May 27, 2015 and 2015-003987 filed on Jan. 13, 2015. The contents of these applications are incorporated herein by reference in their entireties.

BACKGROUND

Technical Field

The present disclosure relates to a dropping rate measuring device, a dropping rate controller, a drip infusion device, and a liquid droplet volume measuring device.

When transfusion or the like is administered to a patient by drip infusion, a nurse needs to adjust the dropping rate (flow rate) of the drip infusion by adjusting the opening of a drip infusion flow path in setting of a transfusion pack. Furthermore, the nurse needs to check the dropping rate periodically because the dropping rate fluctuates due to bending of a tube, or the like, during the drip infusion in some cases.

Known has been a transfusion system that counts the number of liquid droplets dropping from the lower end of a nozzle in a drip infusion cylinder and controls the dropping rate based on the counted number in order to automatically control the above-described dropping rate.

For example, Patent Document 1 (Japanese Patent No. 5131894) discloses a method in which the total amount of drip infusion solution, the droplet amount per predetermined time, and the number of droplets per milliliter are set, the number of times of dropping in a drip infusion cylinder is counted by detecting light emitted from a light emitting diode by a photodiode, and the opening of a conduit connected to the drip infusion cylinder is adjusted using a linear stepping motor (actuator) based on the counted number of times of dropping. Patent Document 3 (Japanese Unexamined Patent Application Publication No. 2012-125450) also discloses a drip infusion monitor device that detects liquid droplets dropping in a light-transmitting drip infusion cylinder by a light emitting element and a light receiving element, and calculates the number of times of dropping and a dropping interval.

However, when the sizes of the liquid droplets are different depending on the viscosities and surface tensions of liquids, an accurate dropping rate cannot be known only by counting the number of times of dropping. That is to say, the number of liquid droplets per milliliter is different depending on liquid types and settings therefore need to be changed in accordance with the liquid type. However, an operation therefor is complicated and there is the risk that the operation is mistakenly performed.

Patent Document 2 (Japanese Patent No. 5583939) discloses a drip infusion detecting device that can not only count the number of times of dropping but also measure the size (volume) of liquid droplets. In the drip infusion detecting device disclosed in Patent Document 2, a two-dimensional image sensor acquires a state until a liquid droplet leaves from the lower end of a nozzle and drops in form of a liquid droplet as a series of moving image or a plurality of pieces of imaged data for each predetermined period of time, specifies image data of the liquid droplet just after dropping from the nozzle, and calculates the volume of the liquid droplet from the image data.

Patent Document 1: Japanese Patent No. 5131894
Patent Document 2: Japanese Patent No. 5583939
Patent Document 3: Japanese Unexamined Patent Application Publication No. 2012-125450

BRIEF SUMMARY

The drip infusion detecting device disclosed in Patent Document 2 has the problem that an expensive camera and the like having high-speed image processing capability (for example, 120 sheets/sec) and a large field view are necessary in order to properly provide image data of the liquid droplet just before dropping from the nozzle and the image data of the liquid droplet just after dropping.

The present disclosure has been made in view of the above-described problems and the present disclosure provides a dropping rate measuring device, a dropping rate controller, a drip infusion device, and a liquid droplet volume measuring device that can accurately measure a flow rate regardless of a liquid type even when an inexpensive camera and the like are used.

<1>
A dropping rate measuring device for measuring a flow rate of liquid droplets which grow on a lower end of a nozzle and intermittently drop from the lower end of the nozzle, the device including:
   an imaging unit that images a growing liquid droplet which is growing on the lower end of the nozzle at a plurality of time points and acquires a plurality of pieces of image data of the growing liquid droplet; and
   a data processor that calculates the flow rate by analyzing the plurality of pieces of image data acquired by the imaging unit.

<2>
The dropping rate measuring device according to <1>, further including a count unit that detects leaving of the liquid droplets from the lower end of the nozzle and counts the number of times of dropping of the liquid droplets,
   wherein the data processor calculates an estimated volume of a dropping liquid droplet after leaving from the lower end of the nozzle by analyzing the plurality of pieces of image data, and calculates the flow rate from the number of times of dropping and the estimated volume.

<3>
The dropping rate measuring device according to <2>,
   wherein the plurality of pieces of image data are a series of moving image imaged by the imaging unit, and
   the data processor also functions as the count unit by detecting leaving of the liquid droplets from the lower end of the nozzle by analyzing the plurality of pieces of image data, and counting the number of times of dropping of the liquid droplets.

<4>
The dropping rate measuring device according to <2>,
   wherein the count unit includes:
   a light emitting portion which emits light to the liquid droplets; and
   a light receiving portion which detects variation in a transmission amount of the light, shielding of the light, variation in a reflection amount of the light, or variation in refraction of the light by the growing liquid droplet or the dropping liquid droplet, and the light receiving portion detects leaving of the liquid droplets from the lower end of the nozzle.

<5>

The dropping rate measuring device according to any one of <2> to <4>,
wherein the data processor:
creates a circle fitted to the growing liquid droplet in each of the plurality of pieces of image data, and
calculates the estimated volume of the dropping liquid droplet based on at least any one of a radius of the circle and a center position of the circle.

<6>

The dropping rate measuring device according to any one of <2> to <4>,
wherein the data processor:
specifies a contour of the growing liquid droplet in each of the plurality of pieces of image data and calculates a volume of the growing liquid droplet from the contour, and
calculates the estimated volume of the dropping liquid droplet based on the volume of the growing liquid droplet.

<7>

The dropping rate measuring device according to <1>,
wherein the data processor calculates a volume increase speed of the growing liquid droplet by analyzing each of the plurality of pieces of image data, and sets the volume increase speed as the flow rate.

<8>

The dropping rate measuring device according to <7>,
wherein the data processor:
creates a circle fitted to the growing liquid droplet in each of the plurality of pieces of image data, and
calculates the volume increase speed based on a variation amount of at least any one of a radius of the circle and a center position of the circle.

<9>

The dropping rate measuring device according to <7>,
wherein the data processor:
specifies a contour of the growing liquid droplet in each of the plurality of pieces of image data and calculates a volume of the growing liquid droplet from the contour, and
calculates the volume increase speed based on the volume of the growing liquid droplet.

<10>

The dropping rate measuring device according to any one of <1> to <9>, further including an illumination device that illuminates the growing liquid droplet.

<11>

The dropping rate measuring device according to <10>,
wherein the illumination device is a stroboscope which repeatedly emits light at a constant interval.

<12>

The dropping rate measuring device according to <10> or <11>,
wherein the illumination device emits light having a wave length, which is not visible light to human.

<13>

The dropping rate measuring device according to any one of <1> to <12>,
wherein the imaging unit includes an optical filter which cuts at least a partial range of visible light.

<14>

The dropping rate measuring device according to any one of <1> to <13>,
wherein the imaging unit includes a plurality of cameras.

<15>

The dropping rate measuring device according to any one of <1> to <14>,
wherein dynamic portions of the plurality of pieces of image data are extracted by comparing the plurality of pieces of image data and removing portions with no variation among the plurality of pieces of image data by image processing.

<16>

A dropping rate controller for controlling a flow rate of liquid droplets which grow on a lower end of a nozzle and intermittently drop from the lower end of the nozzle, the controller including:
the dropping rate measuring device according to any one of <1> to <15>; and
an adjusting device for adjusting the flow rate based on the flow rate of the liquid droplets, which has been measured by the dropping rate measuring device.

<17>

The dropping rate measuring device according to <2>,
wherein operation of the imaging unit is stopped after the estimated volume of at least one dropping liquid droplet is calculated.

<18>

The dropping rate measuring device according to <17>,
wherein operation of the count unit is stopped before the operation of the imaging unit is stopped and the count unit is operated after the operation of the imaging unit is stopped.

<19>

The dropping rate measuring device according to <17> or <18>,
wherein the operation of the imaging unit is stopped after the estimated volumes of the plurality of dropping liquid droplets are calculated and an average value of the estimated volumes is calculated, and
the flow rate is calculated from the number of times of dropping and the average value of the estimated volumes.

<20>

A dropping rate controller for controlling a flow rate of liquid droplets which grow on a lower end of a nozzle and intermittently drop from the lower end of the nozzle, the controller including:
the dropping rate measuring device according to any one of <17> to <19>; and
an adjusting device for adjusting the flow rate based on the flow rate of the liquid droplets, which has been measured by the dropping rate measuring device,
wherein the adjusting device adjusts the flow rate such that the flow rate before the operation of the imaging unit is stopped is lower than the flow rate after the operation of the imaging unit is stopped.

<21>

A drip infusion device including:
a drip infusion cylinder;
a nozzle for causing liquid droplets to intermittently drop into the drip infusion cylinder;
a tube for discharging the liquid droplets that have dropped into the drip infusion cylinder from the drip infusion cylinder; and
the dropping rate controller according to <16> or <20>.

<22>

The drip infusion device according to <21>,
wherein the drip infusion cylinder is transparent,
the tube is a flexible tube,
the adjusting device includes an actuator, and the adjusting device adjusts the flow rate by pressing a part of the flexible tube from an outside by the actuator to adjust an opening of a flow path in the flexible tube.

<23>

The drip infusion device according to <21> or <22>, wherein the drip infusion cylinder is transparent and the imaging unit images the growing liquid droplet from an outside of the drip infusion cylinder.

<24>

The drip infusion device according to <23>, wherein an inner wall of the drip infusion cylinder has hydrophilic property.

<25>

A liquid droplet volume measuring device for measuring an estimated volume of a dropping liquid droplet after leaving from a lower end of a nozzle for liquid droplets which grow on the lower end of the nozzle and drop from the lower end of the nozzle, the device including:

an imaging unit that images a growing liquid droplet which is growing on the lower end of the nozzle at a plurality of time points and acquires a plurality of pieces of image data of the growing liquid droplet; and a data processor that calculates the estimated volume of the dropping liquid droplet by analyzing the plurality of pieces of image data acquired by the imaging unit.

The present disclosure can accurately measure a flow rate regardless of a liquid type even when an inexpensive camera and the like are used because the size (volume) of a liquid droplet can be measured by imaging a growing liquid droplet the movement speed of which is lower than that of a dropping liquid droplet.

BRIEF DESCRIPTION OF THE SEVERAL VIEWS OF THE DRAWINGS

FIG. 3 is a schematic view illustrating an example of image data of a liquid droplet in the first embodiment.

FIG. 4 is a schematic view illustrating another example of the image data of the liquid droplet in the first embodiment.

FIGS. 31A-31C are front views illustrating an application of the first configuration example of the sixth embodiment.

FIG. 32 is a perspective view illustrating the configuration in a second configuration example of the sixth embodiment.

FIGS. 33A and 33B are side views illustrating the configuration in the second configuration example of the sixth embodiment.

DETAILED DESCRIPTION

Figure 1:
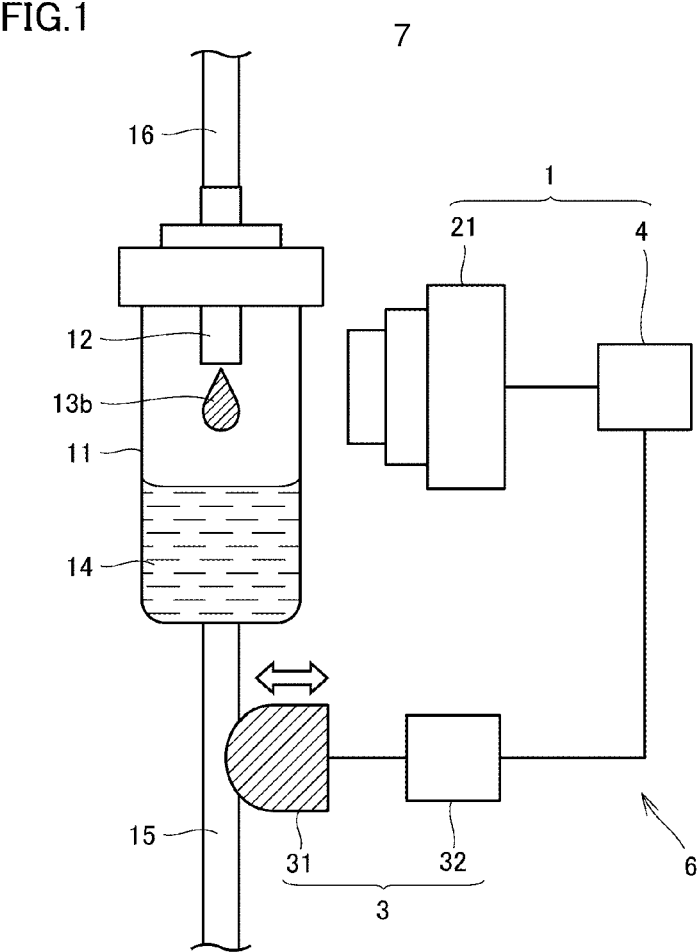
FIG. 1 is a schematic view illustrating the configuration in a first embodiment.

Hereinafter, embodiments of the present disclosure will be described with reference to the drawings. In the drawings, the same reference numerals denote the same portions or equivalent portions. Dimensional relations such as lengths, widths, thicknesses, and depths are appropriately changed for making the drawings obvious and simple and do not indicate actual dimensional relations.

The respective embodiments are examples and it is needless to say that partial replacements or combinations of configurations described in different embodiments can be made. In a second embodiment and subsequent embodiments, description of matters which are common to those in a first embodiment are omitted and only different points are described. In particular, the same action effects by the same configurations are not referred in each embodiment.

First Embodiment

<Drip Infusion Device>

A drip infusion device 7 in the embodiment mainly includes a drip infusion cylinder 11, a nozzle 12 for causing liquid droplets to intermittently drop in the drip infusion cylinder 11, a tube 15 for discharging the liquid droplets which have dropped in the drip infusion cylinder 11 from the drip infusion cylinder 11, and a dropping rate controller 6 with reference to FIG. 1. It should be noted that the dropping rate controller 6 will be described in detail later.

The nozzle 12 (dropping nozzle) for causing liquid droplets 13 to intermittently drop is provided in an upper portion of the drip infusion cylinder 11. The inside of the nozzle 12 communicates with the inside of the drip infusion cylinder 11.

The drip infusion cylinder 11 is arranged at, for example, a halfway position on a transfusion line to a patient from a transfusion bag hung by a stand at a higher position than the patient. The upper end of the nozzle 12 is connected to a tube 16 configuring the transfusion line at the transfusion bag side. The lower end of the drip infusion cylinder 11 is connected to the tube 15 configuring the transfusion line at the patient side.

A transfusion (liquid medicine) in the transfusion bag flows downward in the tube 16 with gravity force and reaches the inside of the nozzle 12. Then, a liquid droplet 13a grows on the lower end of the nozzle 12 (see FIG. 3). When the liquid droplet 13a grows to a predetermined size, it falls (drops) in the drip infusion cylinder 11 (see FIG. 4). It should be noted that the growing liquid droplet 13a can be imaged from the outside because the drip infusion cylinder 11 is transparent.

The drip infusion device in the embodiment can feed the transfusion at an accurate flow rate (flow velocity) for an accurate time regardless of a liquid type in comparison with the existing drip infusion device.

Usage of a transfusion system of a type using a transfusion pump enables the flow rate to be controlled accurately. However, mechanisms of the pump and the like are complicated and a device is increased in size and weight, resulting in increase in the cost. By contrast, the drip infusion device in the embodiment requires no pump and a device can be thereby reduced in size and weight, thereby achieving reduction in the cost.

When the transfusion is forcibly fed with the pump, there is the risk that the transfusion is fed even if an injection needle at a tip of the transfusion line is not inserted into a predetermined position in a blood vessel. On the other hand, the drip infusion device decreases this risk.

<Dropping Rate Controller>

The dropping rate controller 6 is a device for controlling the flow rate of the liquid droplets which grow on the lower end of the nozzle 12 and intermittently drop from the lower end of the nozzle 12. The dropping rate controller 6 includes a dropping rate measuring device 1 and an adjusting device 3. Note that the flow rate (dropping rate) is the amount of liquid droplets which drop per unit time.

The adjusting device 3 is a device for adjusting the dropping rate of the liquid droplets based on the dropping rate (dropping speed) measured by the dropping rate measuring device 1. The adjusting device 3 includes an actuator 31 and a controller 32. The dropping rate measuring device 1 will be described in detail later.

The actuator 31 can change the width (opening) of the flow path in the tube 15 by, from the outside, pressing and crushing the tube 15 connected at the downstream side (lower side) of the drip infusion cylinder 11. The tube 15 is a flexible tube made of a flexible material such as resin. For example, a linear stepping motor can be used as the actuator 31. The linear stepping motor can crush the flexible tube 15 to a desired width to change a flow path resistance of the tube 15, thereby controlling the flow rate. The controller 32 includes, for example, an encoder, and can accurately control the position of the actuator 31 by the encoder.

When the dropping rate of the liquid droplets, which has been measured by the dropping rate measuring device 1, is higher than a target value, the controller 32 drives the actuator 31 such that the dropping speed is decreased by increasing the crushing amount (decreasing the opening) of the flexible tube. By contrast, when the dropping rate of the liquid droplets, which has been measured by the dropping rate measuring device 1, is lower than the target value, the controller 32 drives the actuator 31 such that the dropping speed is increased by reducing the crushing amount (increasing the opening) of the flexible tube.

The above-described adjustment of the dropping rate by the adjusting device 3 is not required to be performed all the time and may be performed periodically with an interval. The periodical adjustment can reduce measuring time by the dropping rate measuring device 1 and driving time of the actuator 31, thereby reducing power consumption.

The target value (set flow rate) needs not to be constant and may vary in an allowable range in consideration of remaining time for finishing the drip infusion for a desired period of time and an estimated integrated flow rate (dropped total amount) until then in halfway of the drip infusion, for example.

The dropping rate controller in the embodiment can automatically control the administration speed of the transfusion or the like accurately. This control reduces a burden involving periodical check of the drip infusion state on a nurse or the like.

<Dropping Rate Measuring Device (Liquid Droplet Volume Measuring Device)>

The dropping rate measuring device 1 is a device for measuring the flow rate of the liquid droplets which grow on the lower end of the nozzle and intermittently drop from the lower end of the nozzle. The dropping rate measuring device 1 includes a camera 21 (imaging unit) and a data processor 4 connected to the camera 21.

The camera 21 (for example, a two-dimensional image sensor) is installed closely to the side surface of the drip infusion cylinder 11 such that a field angle of the camera 21 contains a space around the lower end of the nozzle 12. In this state, the camera 21 can image each growing liquid droplet which grows on the lower end of the nozzle 12 until the liquid droplet drops at a plurality of time points to acquire a plurality of pieces of image data (for example, a series of moving image). It should be noted that "growing" indicates a halfway state in which the liquid droplet is growing on the lower end of the nozzle, that is, a halfway state in which the liquid droplet is gradually increased in size while adhering to the lower end of the nozzle.

Figure 2:
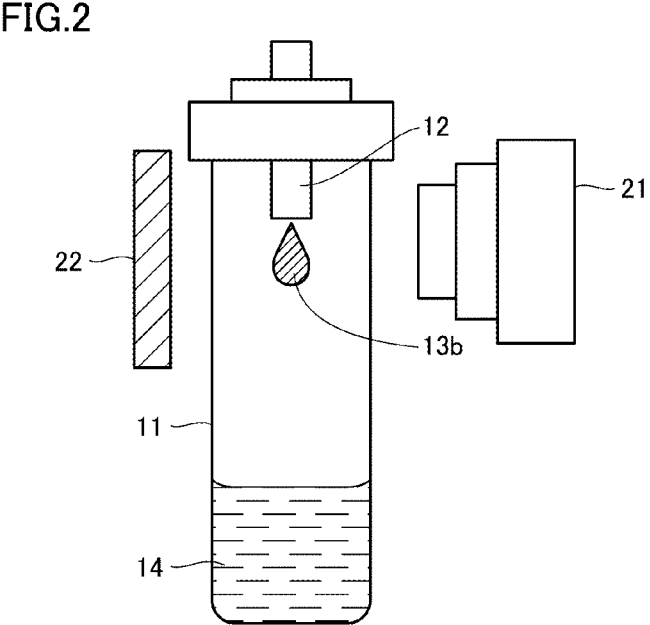
FIG. 2 is a schematic view illustrating the configuration in a variation of the first embodiment.

Furthermore, as a variation of the dropping rate measuring device in the embodiment, an illumination device 22 may be provided at the opposite side to the camera 21 with respect to the drip infusion cylinder 11, as illustrated in FIG. 2. The illumination device 22 can illuminate at least the liquid droplet which is growing on the lower end of the nozzle 12.

With the illumination device 22, a liquid pool can be reliably imaged by illumination even with disturbance such as external light. Furthermore, even with disturbance such as vibration, images with few slurs can be provided because the illumination can increase a shutter speed per image. Therefore, an abnormal image under vibration or the like can be easily determined.

A stroboscope which repeatedly emits light at a constant interval can be used as the illumination device 22. In this case, even with the disturbance such as the external light, the liquid droplet can be imaged more reliably by stroboscopic illumination. Furthermore, images with fewer slurs can be provided because the stroboscopic illumination can further increase the shutter speed per image.

When the illumination device 22 is used, the camera 21 has sensitivity to a wave length of the light that is emitted from the illumination device 22. When the illumination device 22 is, for example, a surface emitting infrared LED illumination, the camera 21 has sensitivity to a wave length of infrared rays. Usage of the infrared LED illumination prevents the illumination device 22 from emitting dazzling light even when a patient is subjected to the drip infusion at night or the like.

When the illumination device 22 is, for example, the surface emitting infrared LED illumination, a filter (not illustrated) which cuts light having a shorter wave length than that of the infrared rays, such as visible light, may be provided at the front side (the drip infusion cylinder 11 side) of the camera 21. The filter can cut unnecessary light.

Regardless of whether the illumination device 22 is used, the camera 21 may include an optical filter which cuts at least a partial range of the visible light.

Although the illumination device 22 emits light from the rear side of the liquid droplet (at the opposite side to the camera 21) in this example, the position of the illumination device 22 is not limited thereto. For example, the illumination device 22 may emit the light from the same side as the camera 21 with respect to the liquid droplet or emit the light from an oblique direction with respect to a straight line connecting the lower end of the nozzle 12 and the camera 21.

The data processor 4 calculates the dropping rate by analyzing the plurality of pieces of image data acquired by the camera 21.

FIG. 3 illustrates an example of image data acquired by the camera 21 during growth of the growing liquid droplet 13*a* on the lower end of the nozzle 12. FIG. 4 illustrates an example of image data acquired by the camera 21 immediately after the liquid droplet starts dropping.

It should be noted that the image as in FIG. 4 cannot always be acquired at any time in dropping. A dropping liquid droplet 13*b* is not imaged or only an upper part of the dropping liquid droplet 13*b* is imaged in some cases because a frame rate of the camera 21 is limited.

Figure 5:
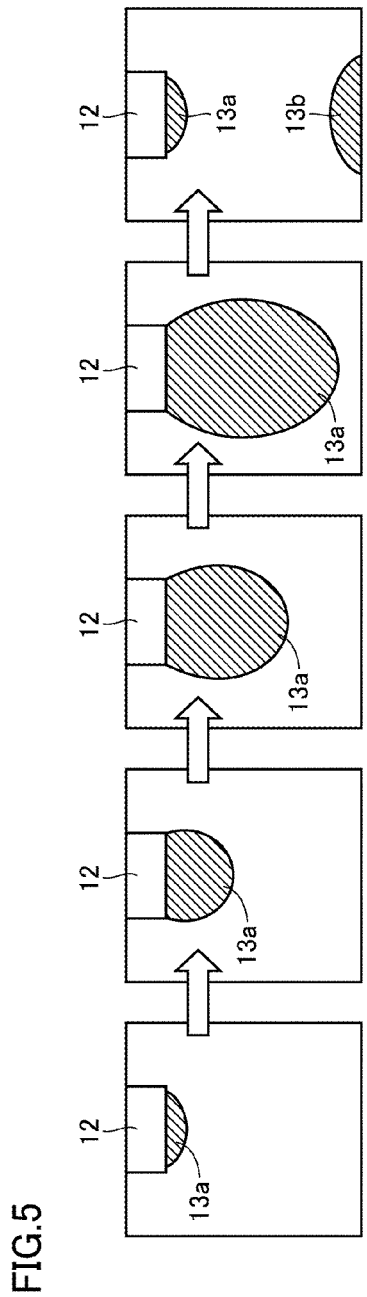
FIG. 5 is a schematic view illustrating an example of a plurality of pieces of image data of the liquid droplet in the first embodiment.
Figure 6:
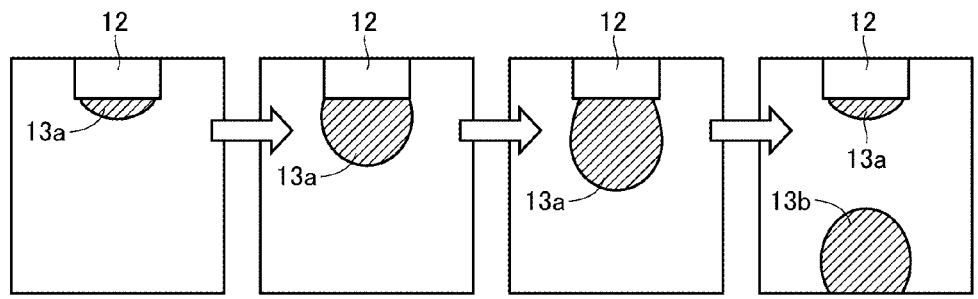
FIG. 6 is a schematic view illustrating another example of the plurality of pieces of image data of the liquid droplet in the first embodiment.

As illustrated in FIG. 5 and FIG. 6, a state in which the liquid droplet 13*a* is gradually increased in size can be imaged by imaging, by the camera 21, the growing liquid droplet which is growing on the lower end of the nozzle 12 at a plurality of time points and acquiring the plurality of pieces of image data of the growing liquid droplet. FIG. 5 illustrates an example when liquid having relatively low viscosity and relatively high surface tension is used. FIG. 6 illustrates an example when liquid having relatively high viscosity and relatively low surface tension is used. In the example of FIG. 5, the size of the dropping liquid droplet 13*b* is relatively larger.

Figure 7:
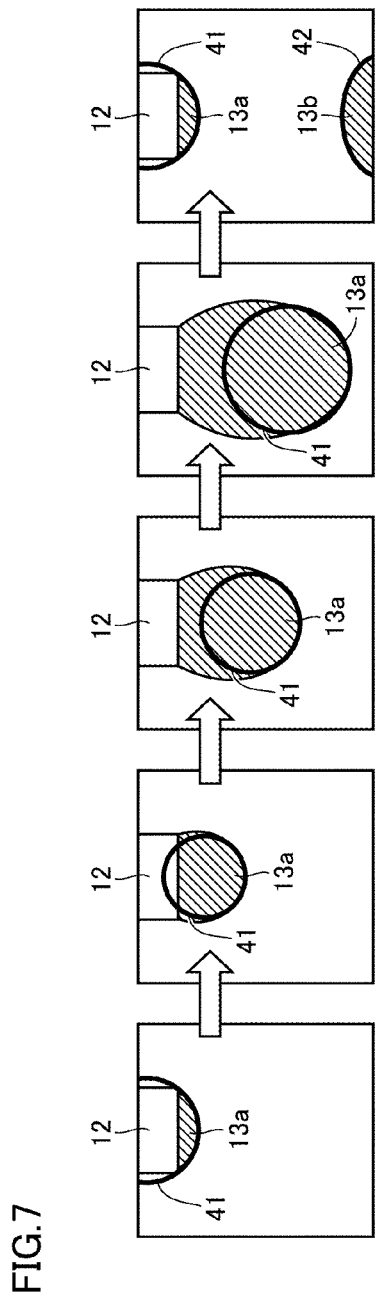
FIG. 7 is a schematic view illustrating circles fitted to the liquid droplet in the plurality of pieces of image data of the liquid droplet illustrated in FIG. 5.
Figure 8:
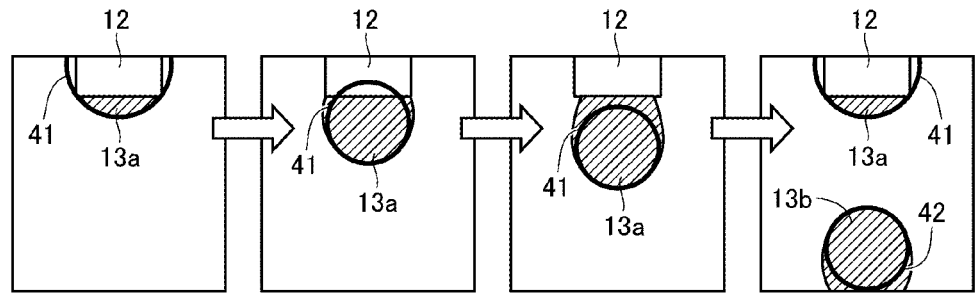
FIG. 8 is a schematic view illustrating circles fitted to the liquid droplet in the plurality of pieces of image data of the liquid droplet illustrated in FIG. 6.

FIG. 7 and FIG. 8 are schematic views indicating circles 41 created (detected) by the Hough transformation using the data processor 4 in the series of growth images of the liquid droplets as illustrated in FIG. 5 and FIG. 6, respectively. By using an image processing technique such as the Hough transformation, a circular arc portion including the lower end of the growing liquid droplet 13*a* can be detected to create the circle fitted to the circular arc portion.

When focusing on the center positions of the circles 41, the center positions gradually move downward along the growth of the liquid droplet 13*a*. After the liquid droplet drops, the center position of the circle 41 returns to an upper position. Accordingly, occurrence of dropping can be determined based on detection of the upward movement of the center position of the circle 41. Based on the determination, the data processor 4 can count the dropping from the pieces of image data.

With the Hough transformation, the dropping liquid droplet 13*b* is detected as a circle 42 in some cases. In this case, continuity of numerical values (indicating the center position of the circle 41, or the like) is lost, thereby being capable of determining that the detection is abnormal. It is sufficient that the image data acquired at this time is not used.

Comparison between FIG. 7 and FIG. 8 indicates that the radii of the detected circles are increased along the growth of the liquid droplet 13*a* in FIG. 7 whereas they are not increased so much in FIG. 8. Thus, the size (volume) of the dropping liquid droplet 13*b* can be estimated using variation in the radius of the detected circle in one cycle from dropping to subsequent dropping. That is to say, by acquiring relations between variations in the radius and the sizes of the liquid droplets for various types of liquids by experiments in advance, the volume of the dropping liquid droplet 13*b* can be estimated by referring thereto.

It should be noted that "dropping" indicates a state before the liquid droplet makes contact with another liquid (for example, a liquid pool 14 in the drip infusion cylinder 11) or solid after leaving the lower end of the nozzle.

Moreover, comparison between FIG. 7 and FIG. 8 indicates that the center positions of the detected circles largely move downward along the growth of the liquid droplet in FIG. 7 whereas they do not move so much in FIG. 8. Thus, the size (volume) of the dropping liquid droplet 13*b* can be estimated using a downward movement distance of the detected circles in one cycle from dropping to subsequent dropping. That is to say, by acquiring relations between the movement distances and the sizes of the liquid droplets for various types of liquids by experiments in advance, the volume of the dropping liquid droplet 13*b* can be estimated by referring thereto. It should be noted that the movement distance of the circles can be derived from the movement distance of the center positions of the circles 41.

When the volume of the dropping liquid droplet 13*b* is estimated by using both of the radii of the circles and the movement distance of the circles as described above, the volume can be estimated more accurately than the case using any one of them.

When the volume of each liquid droplet and the dropping speed (the number of times of dropping per unit time) are known, the dropping rate (flow rate) can be derived by multiplying both of them by each other. Accordingly, in order to measure the dropping rate, the dropping rate measuring device in the embodiment is also required to include a counter (count unit) that detects leaving of the liquid droplets from the lower end of the nozzle and counts the number of times of dropping of the liquid droplets in addition to measurement of the volume of the dropping liquid droplet 13b.

The embodiment has described the above example in which occurrence of the dropping is detected using the pieces of image data by the camera 21, that is, the example in which the data processor 4 also functions as the count unit. This case has the advantage that the count unit is not required to be separately provided.

Figure 9:
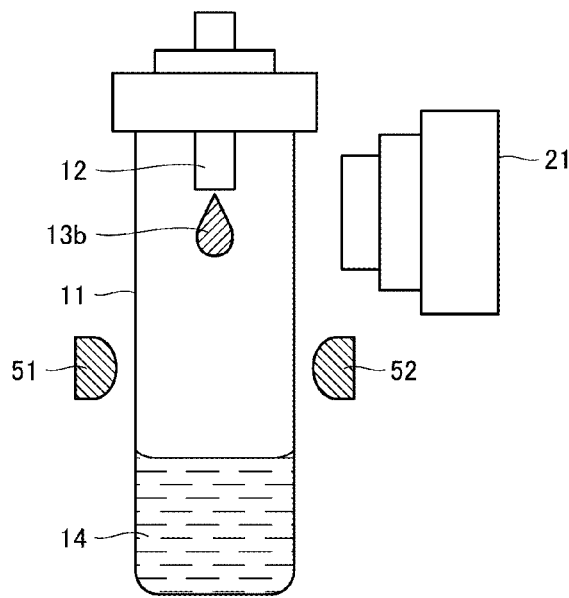
FIG. 9 is a schematic view illustrating the configuration in another variation of the first embodiment.

However, the count unit may be provided separately from the data processor 4. As illustrated in FIG. 9, the count unit may be configured by a light emitting portion 51 and a light receiving portion 52 (for example, a phototransistor) arranged in the vicinity of both of the sides of the drip infusion cylinder 11. The light emitting portion 51 emits light to the dropping liquid droplet 13b. The light receiving portion 52 detects variation in the transmission amount of light or shielding of the light by the dropping liquid droplet 13b, the light being emitted from the light emitting portion 51.

Although the light emitting portion 51 and the light receiving portion 52 are arranged so as to oppose each other with the drip infusion cylinder 11 interposed therebetween in FIG. 9, the arrangement is not limited thereto and the light receiving portion 52 may be arranged so as to detect light emitted from the light emitting portion 51 and reflected by the growing liquid droplet. As a light source of the light emitting portion 51, for example, an infrared LED or a laser of the visible light can be used although it is not particularly limited.

The count unit as described above can detect occurrence of the dropping (leaving of the liquid droplets from the lower end of the nozzle) by, for example, detecting the light shielding by the dropping by the light receiving portion 52 to count the number of times of dropping. The light receiving portion 52 is not limited to detect the light shielding (decrease of the transmission light) by the liquid droplets. Alternatively, the light receiving portion 52 may be configured to be capable of detecting dropping by detecting light emitted from the light emitting portion 51 and reflected by the liquid droplets.

As described above, when the count unit as a different component from the camera 21 (imaging unit) is used, the pieces of image data provided by the camera 21 are not used for counting the number of times of dropping and the moving image needs not to be continuously taken all the time by the camera 21. The size of each liquid droplet is determined by the liquid type and the type of the dropping nozzle. Therefore, it can be considered that the size of the liquid droplet does not vary during a series of drip infusion for one time and grasping thereof once is enough. For example, it is sufficient that the moving image for grasping the size (estimated volume) of the liquid droplet is taken for several seconds or several minutes immediately after the start of the drip infusion or at another appropriate time, or is periodically taken at an interval. Accordingly, a calculation load on a calculator configuring the data processor can be reduced and power consumption of the camera 21 and the illumination device 22 can be reduced, thereby reducing power consumption of the overall system.

Components of the dropping rate measuring device 1 other than the count unit can configure the liquid droplet volume measuring device for measuring the estimated volume of each dropping liquid droplet after leaving the lower end of the nozzle for the liquid droplets which grow on the lower end of the nozzle and drop from the lower end of the nozzle.

Furthermore, in the embodiment, the volume of the dropping liquid droplet 13b is estimated from the radii or the center positions of the circles 41 created by the Hough transformation. However, the estimation method is not limited thereto and the volume of the dropping liquid droplet 13b may be estimated from another analysis result of the pieces of image data.

For example, the volume of the dropping liquid droplet 13b may be estimated from distances between circles fitted to the circular arc portions including the lower end of the growing liquid droplet 13a, which are created by the Hough transformation, and a boundary line (horizontal line) created between the liquid droplet 13a and the lower end of the nozzle 12.

As another method for estimating the volume of the dropping liquid droplet 13b, there is a method in which contours of the growing liquid droplet 13a are specified in the respective pieces of image data, the volumes of the growing liquid droplet 13a are calculated from the contours, and the estimated volume of the dropping liquid droplet 13b is calculated based on the volumes of the growing liquid droplet 13a.

Figure 10:
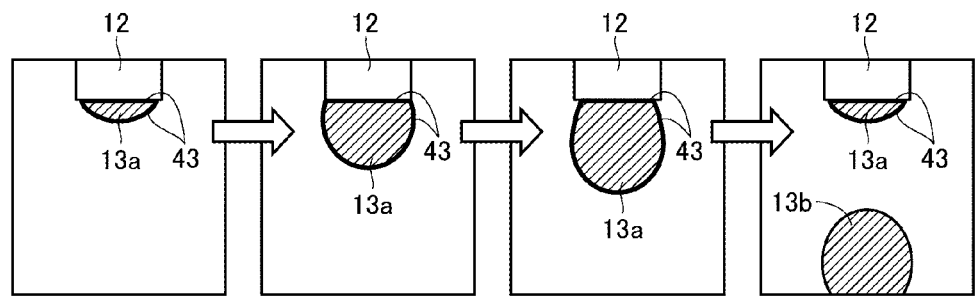
FIG. 10 is a schematic view illustrating contours of a specified liquid droplet in the plurality of pieces of image data of the liquid droplet illustrated in FIG. 6.

FIG. 10 is a schematic view illustrating contours 43 of the liquid droplet 13a, which have been specified (detected) by the data processor, in a series of the pieces of image data of the growing liquid droplet 13a illustrated in FIG. 6. When it is assumed that the liquid droplet 13a has an axially symmetrical shape, three-dimensional volumes thereof can be calculated from two-dimensional images (regions surrounded by the contours 43), thereby calculating the volumes of the liquid droplet 13a in the respective piece of image data.

Figure 13:
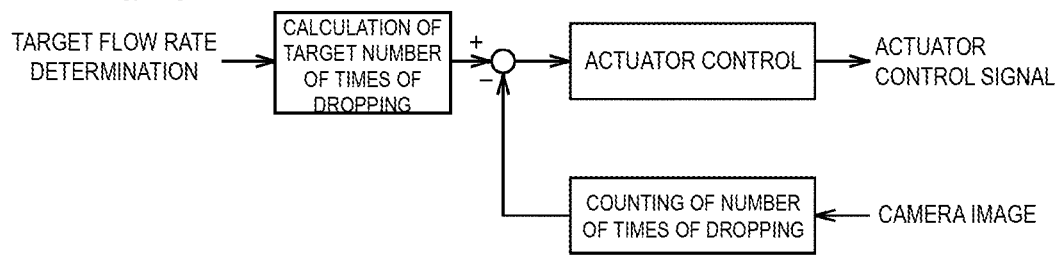
FIG. 13 is a block diagram illustrating an example of flow of control of a dropping rate in the first embodiment.

FIG. 13 is a block diagram illustrating an example of flow of control of the dropping rate in the first embodiment. With reference to FIG. 13, first, a target flow rate (target dropping rate) is determined and the target flow rate is divided by the estimated volume of the dropping liquid droplet (one droplet), which has been measured as described above, to calculate the target number of times of dropping per unit time. On the other hand, the number of times of dropping per unit time is counted as described above from the pieces of image data acquired by the camera 21. The actuator is controlled (for example, PI control) based on a value obtained by subtracting the actually counted number of times of dropping per unit time from the target number of times of dropping per unit time and an actuator control signal is transmitted.

Although the dropping speed (the number of times of dropping per unit time) is controlled in a control system illustrated in FIG. 13, this control is equivalent to control of the flow rate as in a control system illustrated in FIG. 14, which will be described later.

In the embodiment, as "dropping", dropping of the liquid droplets in the drip infusion cylinder 11 in the drip infusion of administering the transfusion or the like to the patient is exemplified. However, "dropping" is not limited thereto and also includes dropping of liquid droplets in the industrial application and the like other than the medical application.

Although the camera 21 is one in the above description, the plurality of cameras 21 may be provided (that is, the imaging unit may include the plurality of cameras) and the flow rate can be derived based on pieces of information (image data) provided by the respective cameras.

In this case, even when a processing result for the image data provided by one camera indicates an abnormal value, the pieces of image data provided by other cameras can be used. Furthermore, processing results for the pieces of image data provided by two cameras can also be averaged, thereby reducing errors or the like depending on measurement positions and measuring the dropping rate more accurately.

Normally, the drip infusion cylinder is transparent and the imaging unit 21 images the growing liquid droplet from the outside of the drip infusion cylinder 11. However, it is also considered that liquid drops that have splashed to the inner wall of the drip infusion cylinder with dropping of the liquid droplets into the liquid pool 14 in the drip infusion cylinder 11 and dusts, fog, and the like that have adhered to the drip infusion cylinder 11 influence image processing results as noise.

To address this, processing of removing portions with no variation may be performed using the plurality of images imaged by the camera 21. This processing can eliminate the influence by the noise due to the dusts, the liquid drops, and the like.

Furthermore, the inner wall of the drip infusion cylinder 11 can have hydrophilic property. For example, hydrophilic processing can be performed on the inner wall of the drip infusion cylinder 11 or hydrophilic coating can be performed thereon. This can suppress, for example, spread-out of the liquid drops that have adhered to the inner wall of the drip infusion cylinder 11 and remaining of the liquid drops with large contact angles on the inner wall of the drip infusion cylinder 11, thereby preventing an optical path of the light to be detected by the camera, the photosensor, and the like from being interfered.

As the hydrophilic coating, there is a method in which the inner wall of the drip infusion cylinder 11 is coated with silica, for example. Furthermore, as the hydrophilic processing, there is a method in which a structure on a mold is transferred onto resin by nanoimprinting or the like. It should be noted that the coating or the processing has compatibility to human bodies.

According to the embodiment, as described above, the volume of each liquid droplet can be measured by imaging the growing liquid droplet 13a the movement speed of which is lower than that of the dropping liquid droplet 13b. Accordingly, even when an inexpensive camera and the like (for example, a camera and a data processing device having image processing capability of approximately 30 sheets/sec) are used, the dropping rate of the liquid droplets can be accurately measured regardless of the liquid droplet type.

Second Embodiment

The embodiment is different from the first embodiment in a point that in a dropping rate measuring device, a data processor analyzes pieces of image data to directly calculate a volume increase speed of a growing liquid droplet without necessarily counting the number of times of dropping and sets the volume increase speed as a flow rate.

In the first embodiment, as described above by referring to FIG. 10, the volumes of the liquid droplet 13a can be calculated from the two-dimensional images (regions surrounded by the contours 43) in the respective pieces of image data.

The volume of the liquid droplet 13a that has adhered to the lower end of the nozzle 12 is largely decreased after the liquid droplet drops. Therefore, one cycle from dropping to subsequent dropping can be cut out from a series of pieces of image data. Among the series of pieces of image data cut out as one cycle from the dropping to the subsequent dropping, the respective volumes of the liquid droplet 13a are calculated from one desired image data and one desired image data at another time. The difference (volume increase amount) between the volumes is calculated and the volume increase amount is divided by a time interval of acquisition of the pieces of image data, thereby deriving the volume change speed. The volume change speed is equal to the dropping rate (flow rate of the drip infusion).

In the embodiment, the dropping rate (flow rate) can be directly derived from the volume increase speed of the growing liquid droplet 13a in the above-described manner. Accordingly, the dropping rate measuring device in the embodiment is advantageous in a point that the count unit which counts the number of times of dropping is not required. Furthermore, in the embodiment, the flow rate can be derived even in a period between the dropping and the subsequent dropping regardless of occurrence of the dropping, thereby performing high-speed control with high accuracy.

Figure 11:
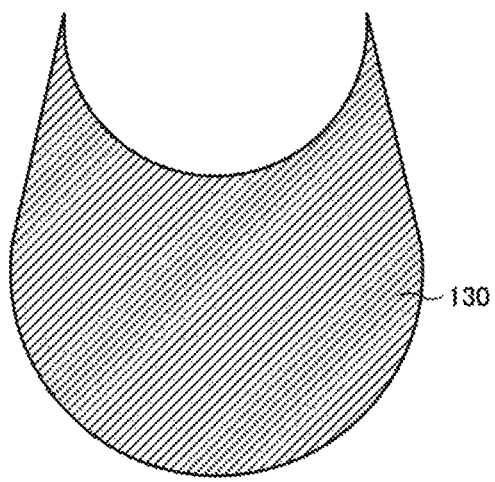
FIG. 11 is a schematic view for explaining a method of calculating the volume of a growing liquid droplet in a second embodiment.
Figure 12:
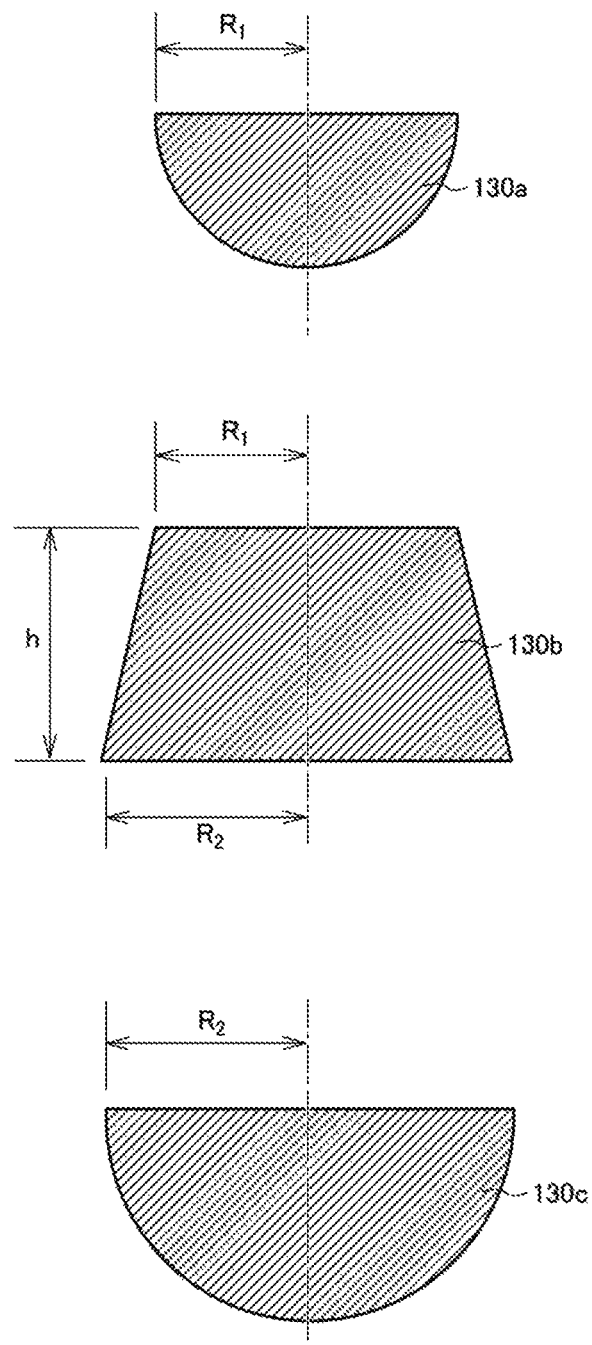
FIG. 12 is another schematic view for explaining the method of calculating the volume of the growing liquid droplet in the second embodiment.

To be specific, for example, when the growing liquid droplet 13a grows to the state of FIG. 3 from the state of FIG. 4, a volume increase part 130 of the liquid droplet 13a during the growth has a shape as illustrated in FIG. 11 roughly. The volume increase part 130 can be approximated by calculation of [a volume B of a truncated cone 130b]+[a volume C of a hemisphere 130c]−[a volume A of a hemisphere 130a] by using the two hemispheres 130a and 130c the truncated cone 130b as illustrated in FIG. 12.

To be specific, an approximated value of the volume increase part 130 can be calculated from an equation expressed by $\pi h(R_1^2+R_1R_2+R_2^2)/3+2\pi R_2^3/3-2\pi R_1^3/3$. $R_1$ is the radius of the hemisphere 130a, $R_2$ is the radius of the hemisphere 130c, and h is the height of the truncated cone 130b.

The hemisphere 130a corresponds to a circle recognized (created) by the data processor initially after dropping and $R_1$ corresponds to the radius of the circle. The hemisphere 130c corresponds to a circle which is recognized by the data processor currently and $R_2$ corresponds to the radius of the circle. h corresponds to a distance between the centers of both of the circles.

This calculation enables the volume of the growing liquid droplet 13a to be derived from the pieces of image data. Therefore, the volume increase speed (dropping rate) of the liquid droplet 13a can also be easily derived momentarily.

Figure 14:
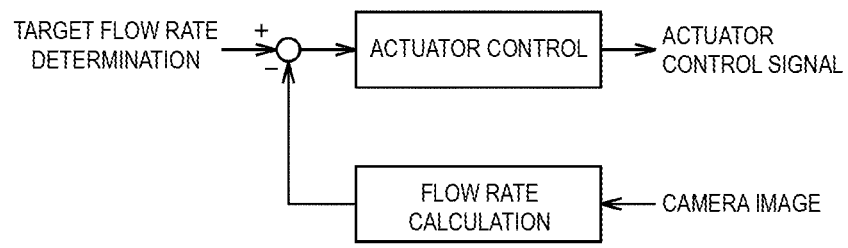
FIG. 14 is a block diagram illustrating an example of flow of control of a dropping rate in the second embodiment.

FIG. 14 is a block diagram illustrating flow of control of the dropping rate in the second embodiment. With reference to FIG. 14, first, a target flow rate (target dropping rate) is determined. On the other hand, the dropping rate (flow rate) is measured from the pieces of image data acquired by the camera 21 as described above. The actuator is controlled (for example, PI control) based on a value obtained by subtracting the actually measured flow rate from the target flow rate and an actuator control signal is transmitted.

Third Embodiment

The embodiment is different from the first embodiment and the second embodiment in a point that operation of the imaging unit 21 is stopped after the estimated volume of at least one dropping liquid droplet is calculated.

The volume of each dropping liquid droplet is stable as long as the type of the liquid droplets (transfusion) and the shape, the material, and the like of the nozzle are the same.

Therefore, after the volume of one dropping liquid droplet is grasped using the imaging unit 21 (camera) initially, the flow rate can be measured by operating only the count unit (dropping detecting unit) while stopping (suspending) the operation of the imaging unit 21 to reduce power consumption. With this, in the embodiment, the power consumption can be reduced in comparison with the case in which the imaging unit 21 is operated all the time.

Figure 15:
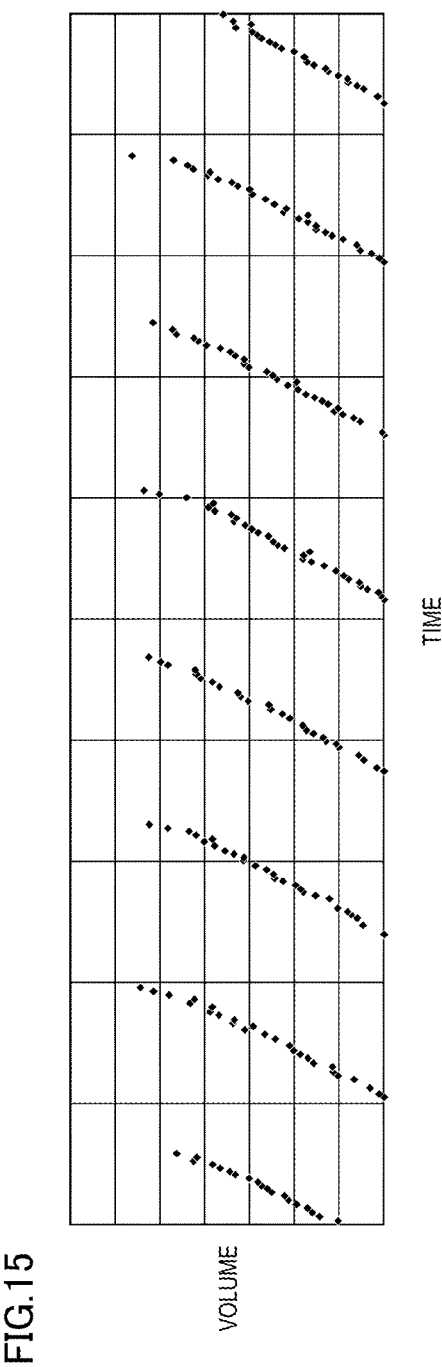
FIG. 15 is a schematic graph illustrating a relation between the volume of the liquid droplet and time for each image data in a third embodiment.

FIG. 15 illustrates a schematic graph plotted while the longitudinal axis is set to the volume of the liquid droplet in each image data and the horizontal axis is set to the time for an example of the case in which the volume of the liquid droplet 13a is calculated from the two-dimensional images (regions surrounded by the contours 43) in the respective pieces of image data as described above by referring to FIG. 10 in the first embodiment. The volume indicated by the longitudinal axis is drawn using, as a reference (zero), the volume when the data processor recognizes the circle initially after the liquid droplet starts growing.

Figure 16:
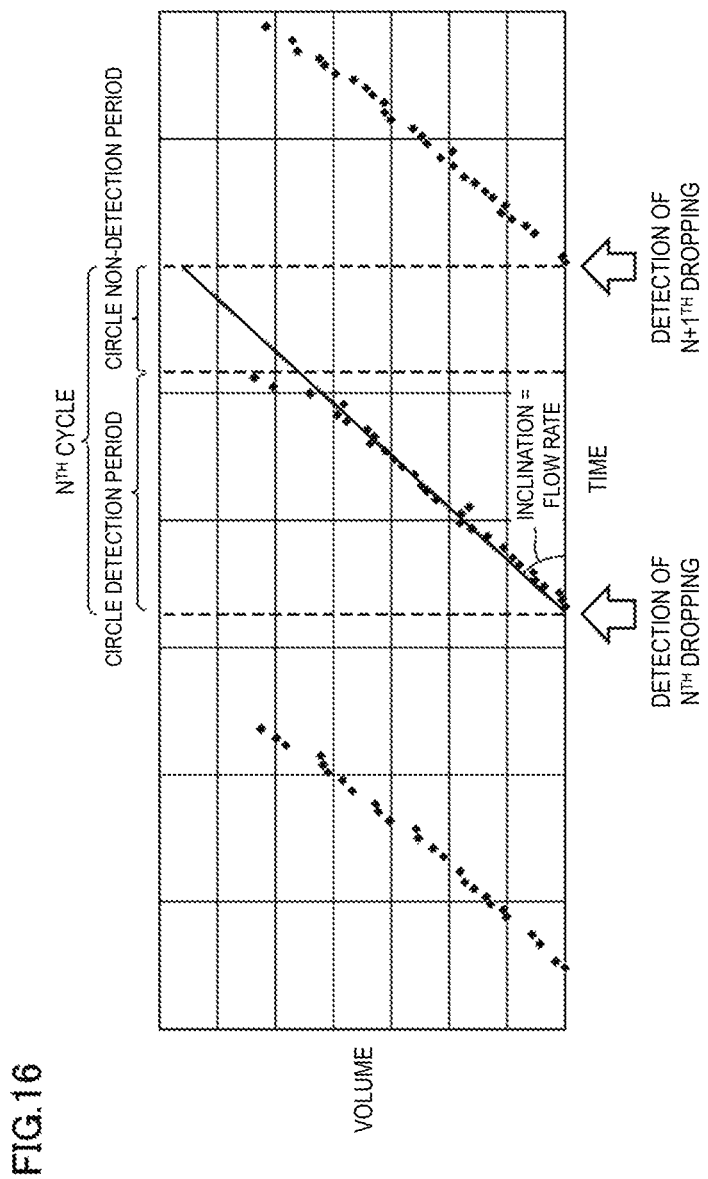
FIG. 16 is a partial enlarged view of FIG. 15.

FIG. 16 is a partial enlarged view of FIG. 15. The state of the liquid droplet in an $N^{th}$ cycle is described with reference to FIG. 16. The $N^{th}$ cycle indicates a period to detection of $N+1^{th}$ dropping from detection of $N^{th}$ dropping. As illustrated in FIG. 16, the $N^{th}$ cycle is composed of a circle detection period and a circle non-detection period. The circle detection period is a period in which the growing liquid droplet is recognized as the circles and the circle non-detection period is a period in which the growing liquid droplet is too small to be recognized as the circle.

A regression line can be drawn by a least-square method for the plot of the $N^{th}$ cycle in FIG. 16. The inclination of the regression line indicates the volume increase per unit time, that is, the flow rate of the liquid droplets.

Dropping of the liquid droplet occurs in halfway of the $N^{th}$ cycle at the time corresponding to the boundary between the circle detection period and the circle non-detection period. Even in the circle non-detection period, it is considered that liquid is continuously supplied to the liquid droplet from the upstream side at a substantially constant flow rate and the liquid droplet continuously grows. Therefore, the volume of the liquid droplet that drops each time can be calculated by multiplying a time of one cycle (dropping cycle) including both of the circle detection period and the circle non-detection period by the flow rate derived from the inclination of the regression line.

It may be considered that the volume of one dropping liquid droplet, which is derived as described above, is basically constant as long as the type of the liquid droplet (transfusion) and the shape, the material, and the like of the nozzle are the same. It is also considered that the volume of one droplet does not vary even when the flow rate and the number of times of dropping per unit time vary with factors such as a positional relation between the transfusion bag and the patient during the drip infusion and routing of the tube.

Accordingly, the imaging unit 21 is not necessarily required to continuously acquire the pieces of image data after the volume of one liquid droplet is derived from the pieces of image data acquired by the imaging unit 21. By operating only the count unit to measure the dropping speed, the flow rate can be calculated by multiplying the derived volume by the dropping speed.

Figure 17:
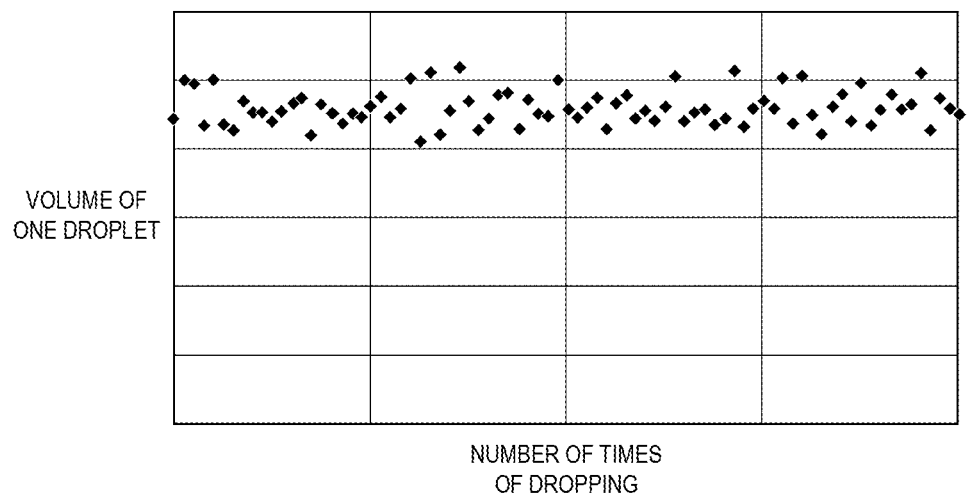
FIG. 17 is a schematic graph illustrating a volume of one liquid droplet, which has been derived by a plurality of number of times of dropping, in the third embodiment.

As is described more properly, as illustrated in FIG. 17 as an example, the volumes of every one-liquid droplets, which are derived by a plurality of times of dropping, slightly vary but an average value thereof is kept to be a substantially constant value. Accordingly, the flow rate can be measured with higher accuracy while reducing power consumption in the following manner. That is, the volumes of one-droplets are derived by the plurality of times of dropping and an average value thereof (average volume of one-droplets) is calculated. After that, the operation of the imaging unit 21 is stopped and the flow rate is calculated based on the average volume.

First Configuration Example

Next, an example (first configuration example) of the specific configurations of the dropping rate measuring device and the like in the embodiment will be described.

Figure 18:
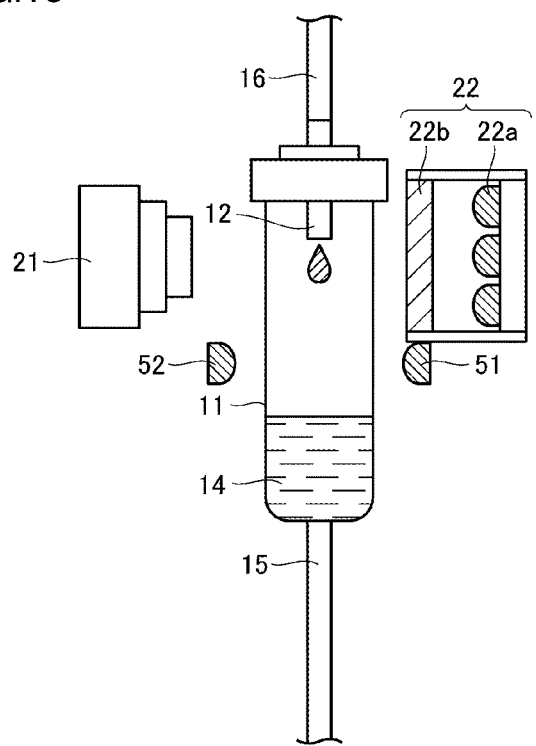
FIG. 18 is a schematic view illustrating the configuration of a dropping rate measuring device in a first configuration example of the third embodiment.

In the dropping rate measuring device in the first configuration example, the illumination device 22 (surface emitting infrared LED illumination) is arranged at the lateral side (right side in the drawing) of the drip infusion cylinder 11, as illustrated in FIG. 18. The illumination device 22 includes a plurality of infrared LEDs 22a mounted on a substrate and a diffusion plate 22b arranged at the drip infusion cylinder 11 side with a predetermined distance from the infrared LEDs 22a.

Furthermore, the camera 21 that can detect the near infrared light is arranged at the opposite side (left side in the drawing) to the illumination device 22 with respect to the drip infusion cylinder 11. The camera 21 can image the liquid droplets growing on the lower end of the nozzle 12, which has been illuminated by the illumination device 22, as a moving image.

The light emitting portion 51 (infrared LED) is arranged under the illumination device 22. The light emitting portion 51 and the light receiving portion 52 (phototransistor) arranged at the opposite side to the light emitting portion 51 with respect to the drip infusion cylinder 11 form a pair to configure a photosensor (photointerrupter). That is to say, when the dropping liquid droplet crosses the vicinity of the front surface of the light receiving portion 52, the light from the light emitting portion 51 is shielded to be weakened, thereby being capable of detecting occurrence of the dropping.

The position of the light receiving portion 52 is desirably a position at which detection sensitivity is high. That is to say, the position of the light receiving portion 52 is not limited to the position in the front of the light emitting portion 51 and may be deviated to a position at which the detection sensitivity is increased. For example, the light receiving portion 52 may be arranged at a slightly higher position than the light emitting portion 51.

Figure 19:
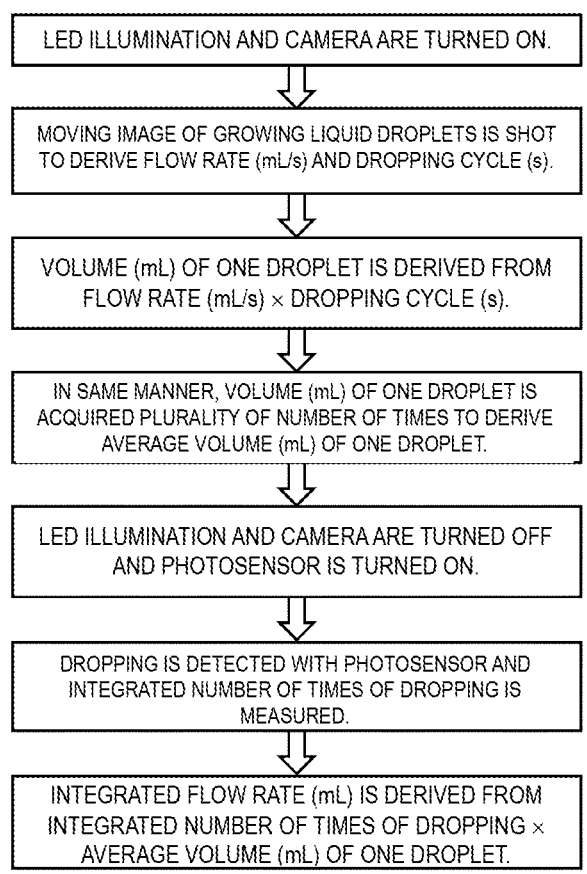
FIG. 19 is a flowchart illustrating flow of operations of the dropping rate measuring device in the first configuration example of the third embodiment.

Next, operations of the dropping rate measuring device in the first configuration example will be described with reference to the flowchart in FIG. 19.

First, the imaging unit 21 (camera) and the illumination device 22 (surface emitting infrared LED illumination) are turned ON to shoot moving image data of the liquid droplets growing on the nozzle lower end. The flow rate of the liquid droplets is directly measured by calculating the volume increase speed of the growing liquid droplet from the obtained moving image data in the same manner as the second embodiment. Furthermore, the dropping of the liquid droplets is detected from the moving image data to derive a dropping cycle (dropping interval).

Thereafter, the volume of one dropping liquid droplet is derived by multiplying the flow rate and the dropping cycle. In the same manner, the volume of one droplet is derived a plurality of number of times and an average value (average volume of one-droplets) thereof is derived. By deriving the average volume of one-droplets in this manner, subsequently, the flow rate, the integrated flow rate, and the like at the current time point can be derived only with the photosensor (count unit) while the camera and the illumination device are turned OFF and the photosensor is turned ON (a camera mode is switched to a photosensor mode).

Then, after the average volume of one-droplets is derived, the camera 21 and the illumination device 22 (LED illumination) are turned OFF in order to reduce power consumption and the count unit (photosensor) configured by the light emitting portion 51 (phototransistor LED) and the light receiving portion (phototransistor) is turned ON instead.

Subsequently, the count unit detects dropping to derive the integrated number of times of dropping. The integrated flow rate can be derived from the integrated number of times of dropping and the average volume of one-droplets. Furthermore, derivation of the dropping cycle by the count unit also enables the flow rate at the current time point to be derived by dividing the average volume of one-droplets by the dropping cycle.

A user can know the flow rate and the integrated flow rate by causing the dropping rate measuring device to display the integrated flow rate, the flow rate, and the like. Therefore, the user can adjust the flow rate to an appropriate value by operating a manual throttle valve (not illustrated).

Figure 20:
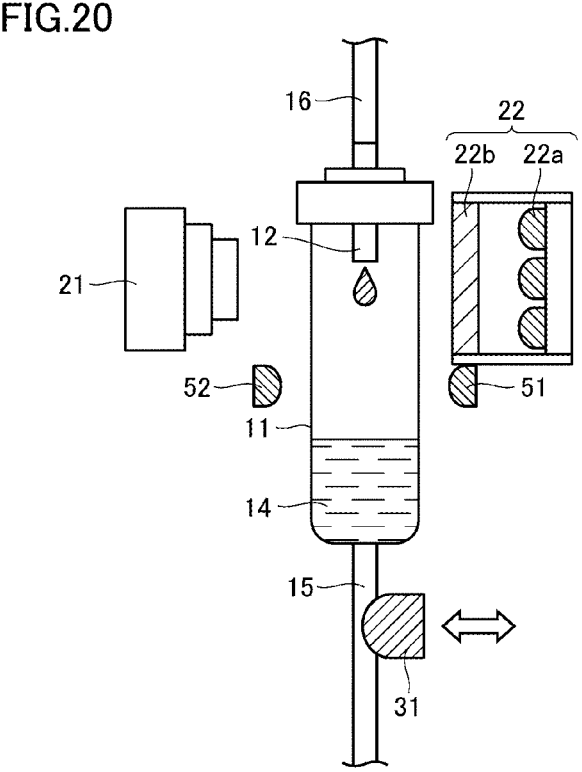
FIG. 20 is a schematic view illustrating the configuration of a dropping rate controller in the first configuration example of the third embodiment.

With reference to FIG. 20, the dropping rate controller (drip infusion controller) in this configuration example further includes an adjusting device (actuator 31 and the like) in addition to the dropping rate measuring device that is same as that in FIG. 18.

Figure 21:
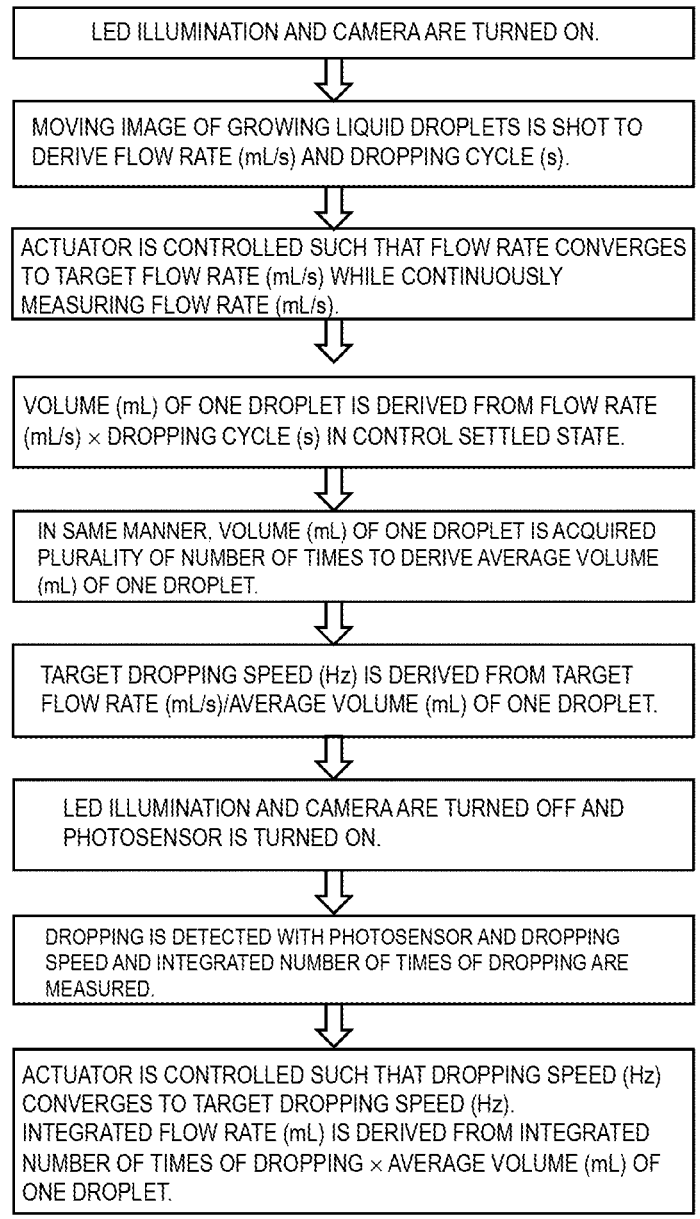
FIG. 21 is a flowchart illustrating flow of operations of the dropping rate controller in the first configuration example of the third embodiment.

Next, operations of the dropping rate controller in the first configuration example will be described with reference to the flowchart in FIG. 21.

First, in the same manner as the dropping rate measuring device in the above-described first configuration example, the flow rate of the liquid droplets is measured. Control is performed so as to achieve a predetermined target flow rate by sequentially feeding back the flow rate data and controlling the actuator 31. Furthermore, dropping of the liquid droplets is detected from the moving image data to derive the dropping cycle.

Then, the actuator 31 is controlled such that the flow rate converges to the target flow rate while continuously measuring the flow rate.

Thereafter, in a state in which the control is settled to some degree, the volume of one dropping liquid droplet is derived by multiplying the flow rate and the dropping cycle. In the same manner, the volume of one droplet is derived a plurality of number of times and an average volume of one-droplets is derived from an average value thereof. Furthermore, the target dropping speed (the number of times of dropping per unit time) can be calculated by dividing the target flow rate by the average volume of one-droplets.

After the target dropping speed is derived, the camera 21 and the illumination device 22 (LED illumination) are turned OFF in order to reduce power consumption and the photosensor is turned ON instead.

Subsequently, the actuator 31 is controlled such that the dropping speed becomes the target dropping speed (a dropping interval becomes a predetermined interval). To be specific, for example, when each dropping interval is deviated from a predetermined target value by equal to or more than 5%, 1 pulse or a plurality of predetermined pulses is(are) output to the stepping motor (actuator 31) to change the crushing amount of the tube. By setting a threshold value of deviation to an appropriate value in this manner, no pulse is output when the deviation is small and the flow rate can be controlled with high accuracy while reducing the power consumption to the minimum necessary.

The integrated flow rate of the liquid droplets can be derived in the same manner as in the dropping rate measuring device in the above-described first configuration example. Therefore, the target dropping speed may be calculated again by recalculating the target flow rate from the difference between the total amount of the liquid droplets that should drop finally (the administration amount of the drip infusion, or the like) and the integrated flow rate and a target time required to finish the dropping, and dividing the target flow rate by the average volume of one-droplets.

Second Configuration Example

Figure 22:
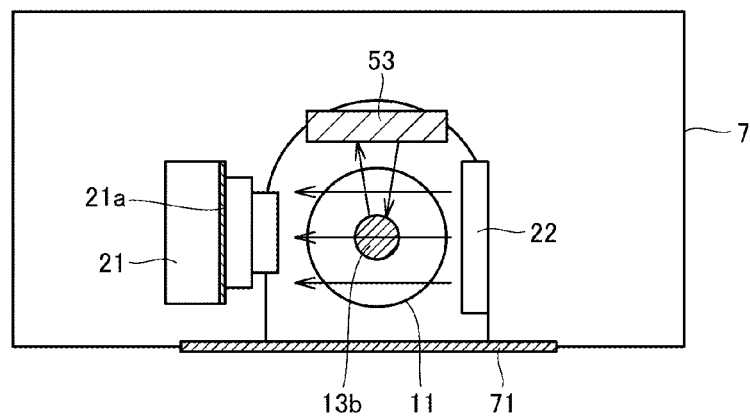
FIG. 22 is a schematic top view illustrating the configuration in a second configuration example of the third embodiment.
Figure 23:
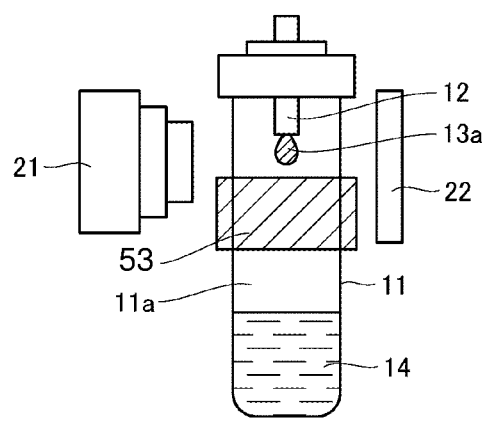
FIG. 23 is a schematic front view illustrating the configuration in the second configuration example of the third embodiment.

Next, another example (second configuration example) of the specific configurations of the dropping rate measuring device and the like in the embodiment will be described. FIG. 22 is a top view of the dropping rate measuring device in the second configuration example. FIG. 23 is a front view when the configuration in a housing 7 illustrated in FIG. 22 is seen from the front side.

In the dropping rate measuring device in the second configuration example of the embodiment, as illustrated in FIG. 22 and FIG. 23, the illumination device 22 (near infrared illumination) and the camera 21 that can detect the near infrared light are arranged in the housing 7 so as to oppose each other with the drip infusion cylinder 11 interposed therebetween.

A space for setting the drip infusion cylinder 11 in the dropping rate measuring device and detaching the drip infusion cylinder 11 from the dropping rate measuring device needs to be set at the near side (lower side in FIG. 22) when seen from the front side of the device. Therefore, a reflection-type photosensor 53 (which is configured by integrating a light emitting element and a light receiving element as one body) of the near infrared light is arranged at the far side (upper side in FIG. 22) when seen from the front side of the device. The reflection-type photosensor 53 can detect variation in the light reflection amount by the growing liquid droplets or the dropping liquid droplets. FIG. 23 illustrates a state in which the reflection-type photosensor 53 is located at the far side of the drip infusion cylinder 11 but the reflection-type photosensor 53 is seen from the front side because the drip infusion cylinder 11 is transparent.

There is, however, the risk that disturbance light including infrared rays is incident from the near side to cause misdetection and malfunction of the camera 21 and the reflection-type photosensor 53 in a state in which none is present at the near side of the device. To address this risk, a door 71 is provided at the near side of the device.

The door 71 can shield the infrared rays and can transmit the visible light. With this, a user can visually check a dropping state in the drip infusion cylinder through the door 71 while shielding the infrared rays from the outside, which cause misdetection of the camera 21 and the reflection-type photosensor 53. In this case, in order to shield the visible light (disturbance) entering from the door 71 in consideration of influence on the camera 21, a visible light cut filter 21a (filter shielding the visible light and transmitting the infrared rays) may be provided in the camera 21.

Figure 24:
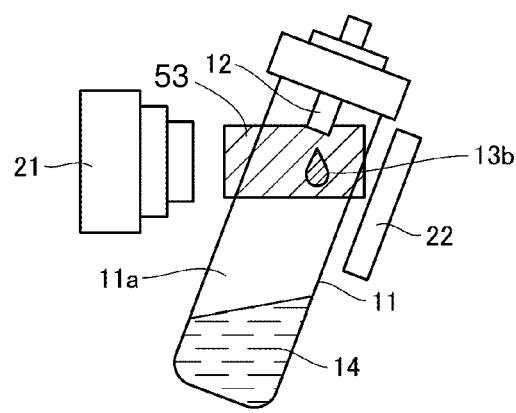
FIG. 24 is a schematic front view illustrating the configuration in a variation of the second configuration example of the third embodiment.

FIG. 24 illustrates the case in which the drip infusion cylinder 11 is obliquely arranged in the front view that is the same as FIG. 23 as a variation of the second configuration example. As illustrated in FIG. 24, with the oblique installation of the drip infusion cylinder 11, the liquid droplets that have dropped do not fall directly to a liquid phase (liquid pool 14) of the transfusion in a lower portion of the drip infusion cylinder but land on the wall surface of the inclined drip infusion cylinder 11 and flow down the slope into the liquid pool 14 in the lower portion of the drip infusion cylinder. This suppresses adherence of the liquid droplets that have splashed to the wall surface of the drip infusion cylinder to prevent liquid drops from adhering to the inner wall of the drip infusion cylinder and shielding the visual fields of the camera 21 and the reflection-type photosensor 53.

In FIG. 23, the height of the reflection-type photosensor 53 is lower than that of the camera. In this case, the camera observes the liquid droplets growing on the lower end of the nozzle to detect the flow rate whereas the reflection-type photosensor 53 detects passage of the dropping liquid droplets to detect dropping. Alternatively, the configuration in which the photosensor detects presence of the growing liquid droplet to detect dropping in a state in which the drip infusion cylinder is arranged perpendicularly may be employed.

FIG. 24 illustrates an arrangement example in which the height of the reflection-type photosensor 53 is the same as that of the camera and the reflection-type photosensor 53 detects presence of the liquid droplet growing on the lower end of the nozzle. Alternatively, the configuration in which the photosensor detects passage of the dropping liquid droplet to detect dropping in a state in which the drip infusion cylinder is arranged obliquely may be employed.

Third Configuration Example

Figure 25:
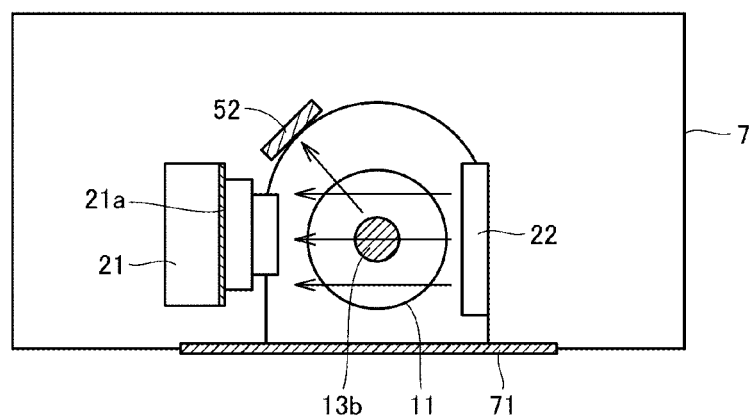
FIG. 25 is a schematic top view illustrating the configuration in a third configuration example of the third embodiment.

Next, another example (third configuration example) of the specific configurations of the dropping rate measuring device and the like in the embodiment will be described. FIG. 25 is a top view of the dropping rate measuring device in the third configuration example.

As illustrated in FIG. 25, the dropping rate measuring device in the third configuration example of the embodiment is different from the second configuration example in a point that only the light receiving portion 52 (photosensor having sensitivity to the near infrared light) is arranged at a position close to the camera 21 at the far side when seen from the device front (door 71) side. Other points thereof are the same as those in the second configuration example.

In the third configuration example, the illumination device 22 is commonly used by the camera 21 and the light receiving portion 52. That is to say, although the light from the illumination device 22 is not directly incident on the photosensor, when the liquid droplet is present on the tip (lower end) of the nozzle 12, a part of the light of the illumination device 22, which has scattered by the liquid droplet, is incident on the light receiving portion 52. That is, the incident light on the light receiving portion 52 becomes strong along the growth of the liquid droplet little by little and the incident light on the light receiving portion 52 becomes weak at the same time as occurrence of dropping. The dropping can be detected based on such variation in the intensity of the incident light on the light receiving portion 52.

In the third configuration example, the illumination device 22 is commonly used by the camera 21 and the light receiving portion 52. Therefore, there is the advantage that the light emitting portion 51 for the light receiving portion 52 is not required to be separately provided. Furthermore, scattering light from the near infrared illumination having a relatively large area, which is arranged for the camera, is used, thereby easily detecting the dropping in comparison with the case of using the reflection-type photosensor.

In the embodiment, after the average volume of the dropping liquid droplets (one-droplets) is derived from the pieces of data in a plurality of cycles using the camera, the camera is turned OFF in order to reduce power consumption and the flow rate is calculated using the light receiving portion 52. Although the near infrared illumination is in the ON state while the camera is in the OFF state in this configuration example, the brightness of the illumination device 22 may be weakened to that necessary for detecting the dropping by the light receiving portion 52 in order to further reduce power consumption.

Fourth Embodiment

The embodiment is different from the third embodiment in a point that the adjusting device (actuator 31) adjusts the flow rate so as to cause the flow rate before the operation of the imaging unit 21 is stopped to be lower than the flow rate after the operation of the imaging unit 21 is stopped. Other points are basically the same as those of the dropping rate controller described with reference to FIG. 20 in the third embodiment.

In the case in which the flow rate (dropping speed) is high, a series of imaging processes involving imaging by the imaging unit 21 (camera), transfer of the pieces of image data to the calculator, image processing, and the like need to be performed at high speed in order to acquire the pieces of image data of the same number of sheets. In general, however, the processes require a large calculation load and the system is increased in cost in order to perform the processes at high speed. When the imaging processes are performed at high speed, the calculation load can be reduced by lowering roughness of pixels but lowering of image precision increases volume measurement errors and is therefore not desirable.

On the other hand, it is sufficient that only the detection of the dropping by the dropping detecting unit (count unit) and the control of the flow rate by the actuator 31 (adjusting device) are performed while the imaging unit 21 is not operated. Therefore, the calculation load is decreased and no problem particularly occurs even when the flow rate is high.

In consideration of the above-described matters, in the embodiment, the flow rate is switched between a state in which the imaging unit 21 images the liquid droplets and a state in which only the count unit is operated after the operation of the imaging unit 21 is stopped. That is to say, the flow rate in the former state is set to be lower than the flow rate in the latter state. The embodiment supposes that the volume of each dropping liquid droplet is basically constant even when the flow rate of the liquid droplets is switched as described above.

With this, in the embodiment, the volume of one dropping liquid droplet can be accurately calculated without necessarily increasing the cost for increasing the speed of the pieces of processing by the imaging unit 21 and the data processor.

Figure 26:
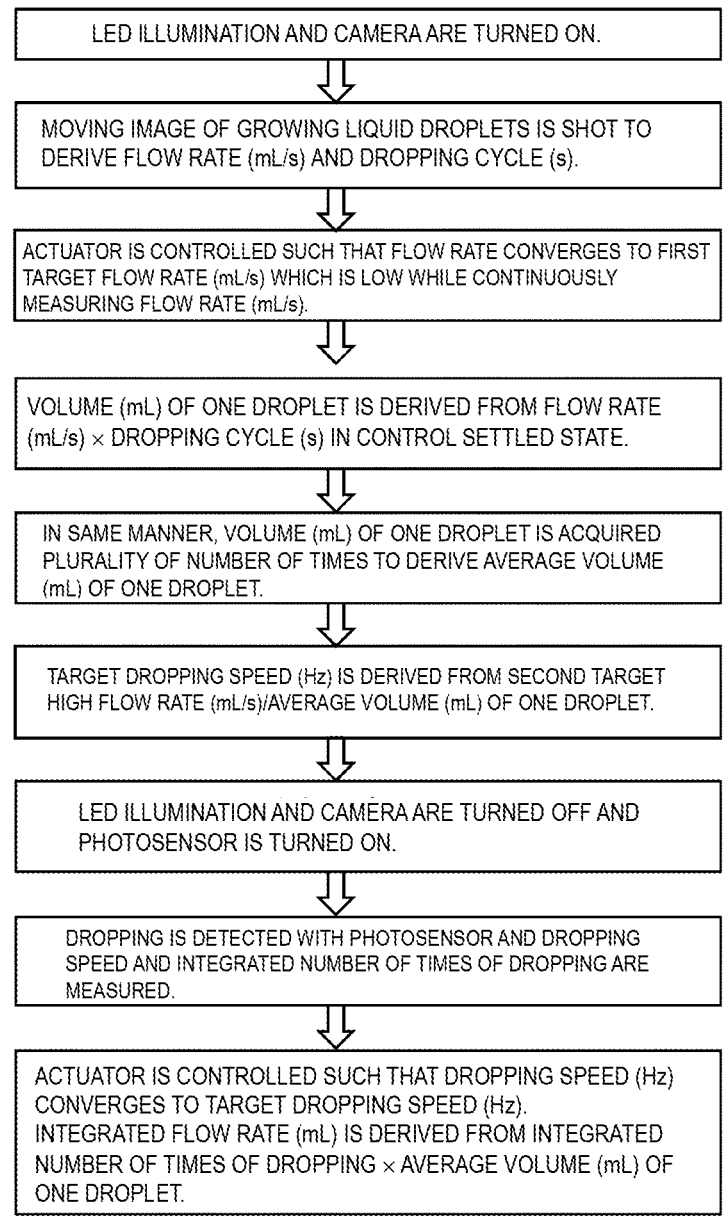
FIG. 26 is a flowchart illustrating flow of operations of a dropping rate measuring device in a fourth embodiment.

FIG. 26 is a flowchart illustrating flow of operations of the dropping rate measuring device in the embodiment.

As illustrated in FIG. 26, processes until the average volume of one-dropping liquid droplets is derived by the imaging unit 21 (camera) are executed in the same manner as those in the third embodiment in a state in which the flow rate of the liquid droplets is set to a first target flow rate which is relatively low (lower than that in a second target flow rate). The target dropping speed for setting the second target flow rate, which is higher than the first target flow rate, is derived by dividing the second target flow rate by the average volume of one-droplets.

Then, after the camera mode is switched into the photosensor mode (the LED illumination and the camera are turned OFF and the photosensor is turned ON), the photosensor detects dropping of the liquid droplets. The actuator 31 is controlled such that the dropping speed converges to the target dropping speed while measuring the dropping speed by the photosensor. Thus, the flow rate of the liquid droplets can be adjusted to the second target flow rate (for example, the flow rate of the liquid droplets actually desired to be controlled).

It should be noted that in the same manner as the third embodiment, the integrated flow rate may be derived by measuring the integrated number of times of dropping from the number of times of dropping detected by the photosensor and multiplying the average volume of one-droplets by the integrated number of times of dropping.

Figure 27:
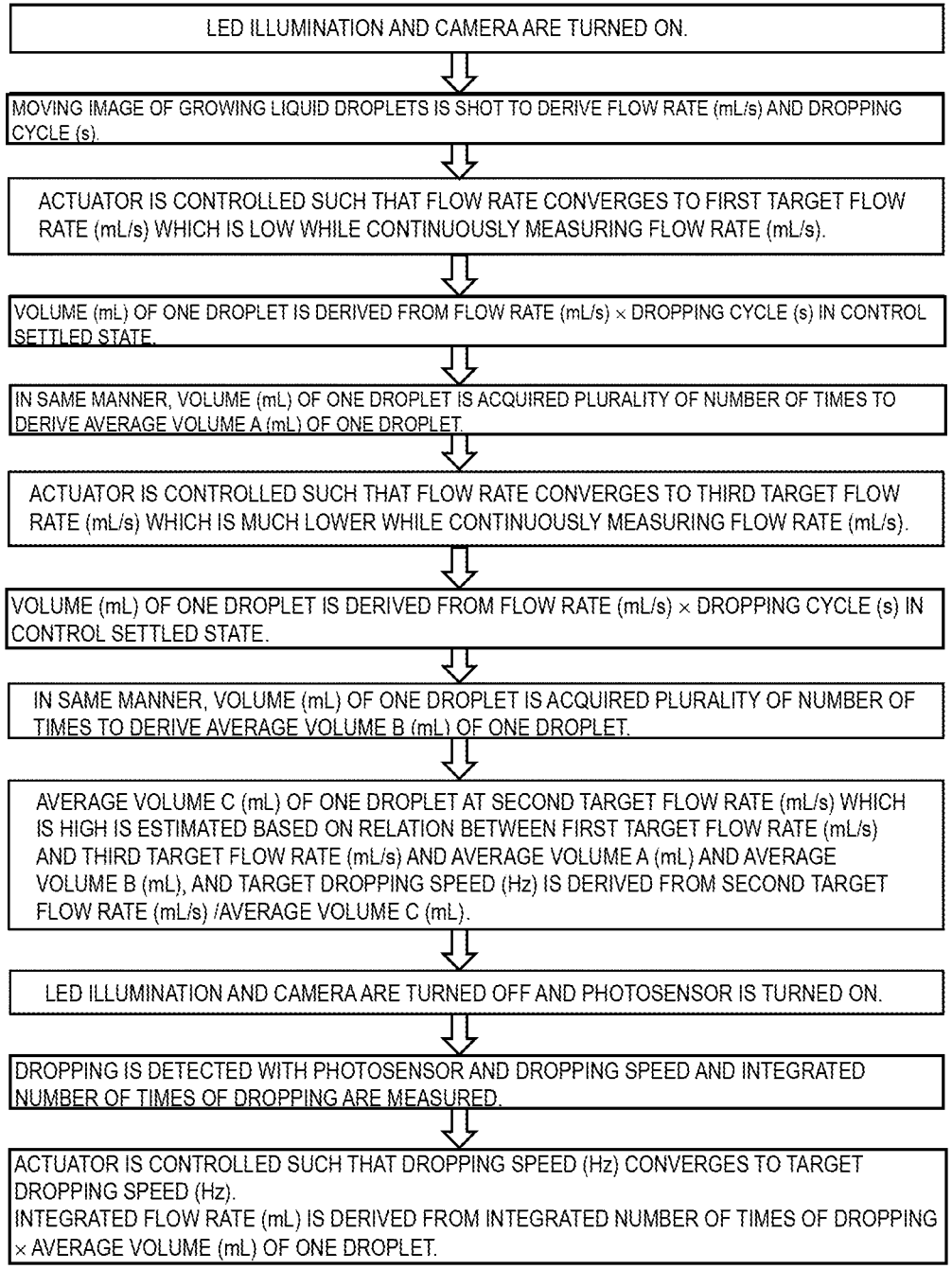
FIG. 27 is a flowchart illustrating flow of operations of a dropping rate measuring device in a variation of the fourth embodiment.

FIG. 27 is a flowchart illustrating flow of operations of the dropping rate measuring device in a variation of the embodiment.

With reference to FIG. 27, in the variation, first, an estimated volume (average volume) A of the dropping liquid droplet is calculated in the state in which the flow rate is set to the first target flow rate which is relatively low. Furthermore, an estimated volume (average volume) B of the dropping liquid droplet is calculated in a state in which the flow rate is set to a third target flow rate which is lower than the first target flow rate. Then, the volume of the dropping liquid droplet in the case in which the flow rate is set to the second target flow rate (which is higher than the first target flow rate and the third target flow rate) is estimated from a relation between the two average volumes A and B when the flow rates are different and the first flow rate and the third flow rate. The target dropping speed is derived based on the estimated volume of the liquid droplet at the second target flow rate estimated in this manner.

In the same manner as the third embodiment, the actuator 31 is controlled such that the dropping speed detected by the photosensor converges to the target dropping speed after the camera mode in which the camera 21 and the illumination device 22 for the camera are turned ON is switched into the photosensor mode in which the photosensor (the light emitting portion 51 and the light receiving portion 52) is turned ON.

In practice, the volume of one dropping liquid droplet possibly varies slightly due to variation in the flow rate while being influenced by viscosity or the like. As in the above-described variation, for at least two different flow rates (any of them can be lower than the flow rate that is actually controlled), a relation (correlation) between the flow rates and the volumes of the liquid droplets is grasped in advance by measuring the volumes of the dropping liquid droplets. Then, the estimated value (corrected value) of the flow rate of the liquid droplet, which is desired to be controlled actually, is derived from the relation, thereby being capable of correcting slight variation in the volume of the liquid droplet due to the variation in the flow rate and measuring and controlling the flow rate more accurately.

Although in the embodiment, the flow rate and the dropping speed are adjusted by the adjusting device (actuator 31) as an example, the flow rate and the dropping speed may be manually adjusted without necessarily using a device such as the actuator.

Fifth Embodiment

In the third embodiment and the like, the camera mode in which the camera 21 and the illumination device 22 for the camera are turned ON and the photosensor mode in which the photosensor (the light emitting portion 51 and the light receiving portion 52) is turned ON are switched. The embodiment is different from the third embodiment and the like in a point that also in the camera mode, dropping is monitored all the time not only by the camera but also by the photosensor.

In the third embodiment, when the dropping rate controller illustrated in FIG. 20 is used, the adjusting device (actuator 31) controlled in accordance with an algorithm adjusts the opening of the tube 15 while measuring the flow rate with the camera 21. Therefore, it is considered that the flow rate of the liquid droplets is adjusted relatively precisely.

On the other hand, when the dropping rate measuring device illustrated in FIG. 18 is used, it is supposed that the flow rate is adjusted by operating, by the user, a manual clip (manual throttle valve) or the like while measuring the flow rate with the camera. There is the possibility that the user sets the flow rate (dropping speed) to be abnormally high by mistake when adjusting the flow rate. In such a case, the flow rate cannot be measured accurately with a camera having a relatively low upper limit of the dropping speed that the camera can measure the flow rate accurately, and there is the risk that the measured value of the flow rate becomes an abnormal value. Due to this, there are the risks that the flow rate cannot be adjusted properly and the volume of one droplet as a reference of calculation of the integrated flow rate or the like is not appropriately set in shift from the camera mode to the photosensor mode.

In the embodiment, in order to prevent these failures, dropping is monitored all the time not only by the camera but also by the photosensor capable of detecting higher-speed dropping than the camera also in the camera mode. The dropping rate measuring device can issue an alarm for an abnormally high dropping speed or the like using a detected value by the photosensor.

However, the illumination device 22 for the camera is in the ON state in the camera mode and there is therefore the risk that the light from the illumination device 22 causes lowering of the sensitivity when the light receiving portion 52 detects shielding of the light from the light emitting portion 51 by the liquid droplets. For this reason, the light from the illumination device 22 for the camera and the light from the light emitting portion 51 for the photosensor can have different peak wavelengths. For example, when the peak wavelength of the sensitivity of the light receiving portion 52 (phototransistor) is 940 nm, the peak wavelength of the illumination device 22 (LED illumination) for the camera is set to 870 nm and the peak wavelength of the light emitting portion 51 (LED) for the photosensor is set to 940 nm. With these settings, the light receiving portion 52 can suppress lowering of the sensitivity when detecting shielding of the light from the light emitting portion 51 by the liquid droplets.

Sixth Embodiment

The embodiment is an embodiment related to a tube clamp for clamping a tube (flexible tube) such as a tube for transfusion.

The tube clamp in the embodiment includes a first lock mechanism for maintaining a state in which the tube is clamped and a second lock mechanism for preventing the first lock mechanism from being released (for preventing the state in which the tube is clamped from being released) (for locking the first lock mechanism). The second lock mechanism is configured so as not to be released after once locking the first lock mechanism.

The tube clamp in the embodiment can prevent medical malpractice and can improve safety because the tube that has been once clamped is not used again. Furthermore, safety is improved because the tube is not released by human-caused carelessness and reuse which is not desired by a manufacturer can be avoided.

Next, the following first to third configuration examples will be described as specific examples of the tube clamp in the embodiment.

First Configuration Example

The tube clamp in the first configuration example of the embodiment will be described with reference to FIG. 28 to FIG. 30C. The tube clamp in the first configuration example is an improved product of an existing one touch-type tube clamp as illustrated in FIG. 28.

Figure 28:
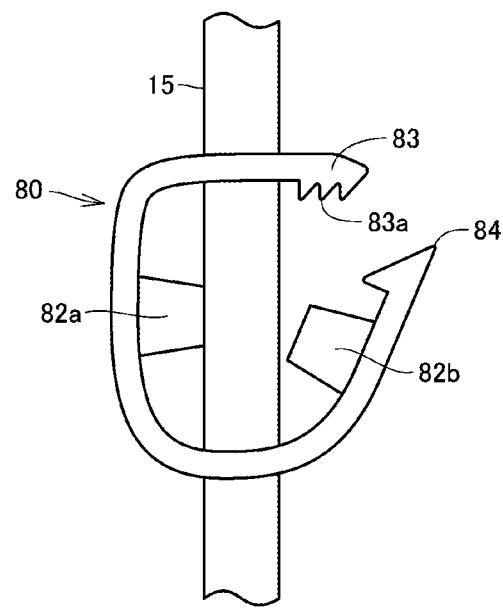
FIG. 28 is a front view illustrating the configuration of an existing one touch-type tube clamp.

As illustrated in FIG. 28, an existing one touch-type tube clamp 80 includes two pressure portions 82a and 82b for clamping the tube 15 and a first lock mechanism (a first sawtooth-shaped portion 83 and a claw 84). The first sawtooth-shaped portion 83 and the claw 84 have flexibility. When the claw 84 is pushed in a sawtooth-shaped projection 83a of the first sawtooth-shaped portion 83, the tip of the claw 84 is hooked thereon to be locked in a state in which an internal space of the tube 15 is closed by the pressure portions 82a and 82b.

In the case of the existing tube clamp 80, however, clamping of the tube 15 can be released again by pushing up the first sawtooth-shaped portion 83 for unlocking and drawing out the claw 84 therefrom. Therefore, when the tube 15 is detached from the dropping rate controller 6, there is the risk that the clamping is released by mistake and liquid in the tube 15 runs down even if the tube 15 is once clamped (is closed) so as not to cause the liquid in the tube 15 to run down. The tube closed by the clamp is normally discarded but there is also the risk that the tube for which clamping has been released by mistake is reused.

Figure 29:
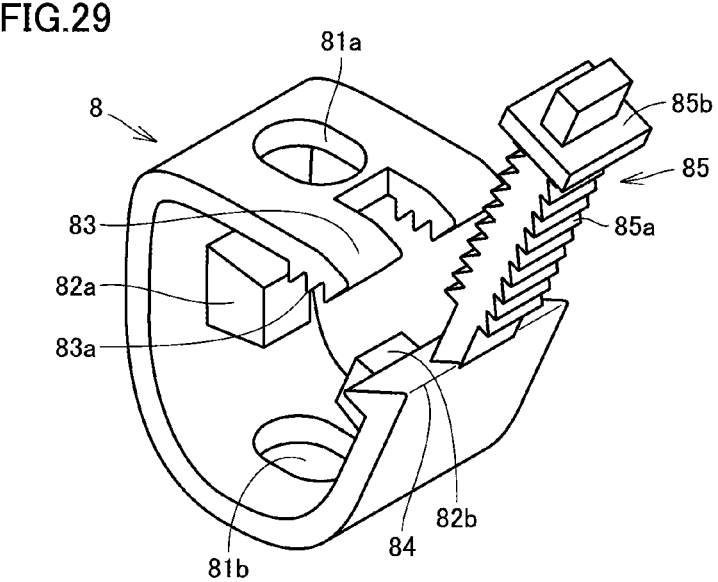
FIG. 29 is a perspective view illustrating the configuration in a first configuration example of a sixth embodiment.

By contrast, as illustrated in FIG. 29, a tube clamp 8 in the first configuration example of the embodiment further includes not only a first lock mechanism (reversible lock mechanism similar to the existing tube clamp 80) for clamping the tube 15 but also an irreversible second lock mechanism (a second sawtooth-shaped portion 85 and a lock member 85b) for preventing the first lock mechanism from being released. The second lock mechanism is configured so as not to be released after being once locked, that is, configured to be capable of making irreversible locking.

Figure 30C:
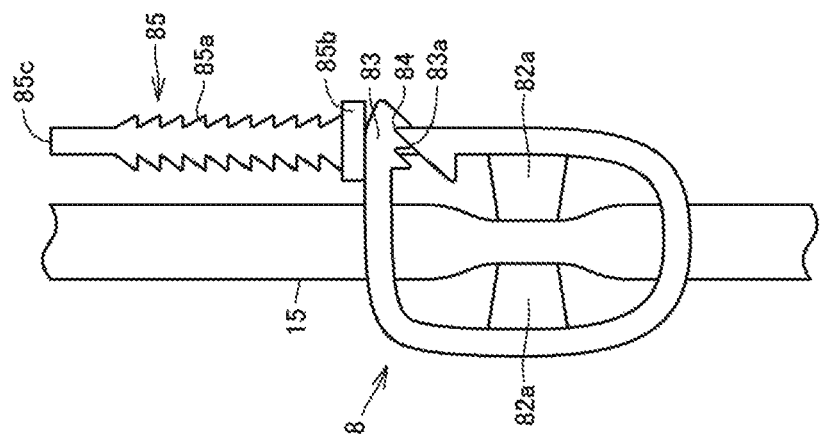
FIGS. 30A-30C are front views illustrating a usage state of the first configuration example of the sixth embodiment.
Figure 30B:
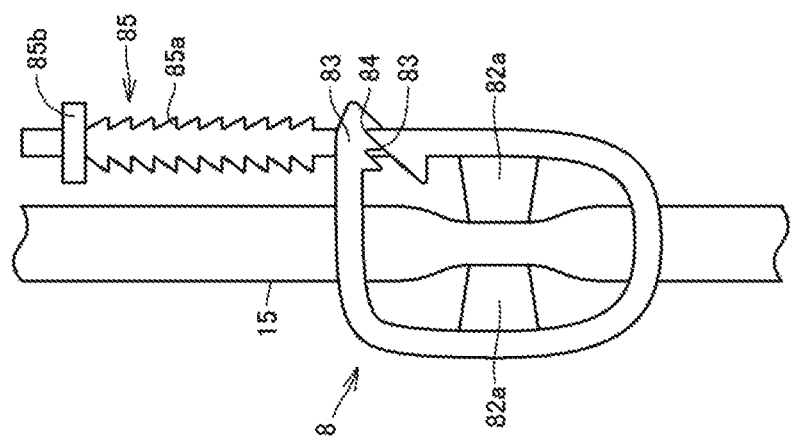
Figure 30A:
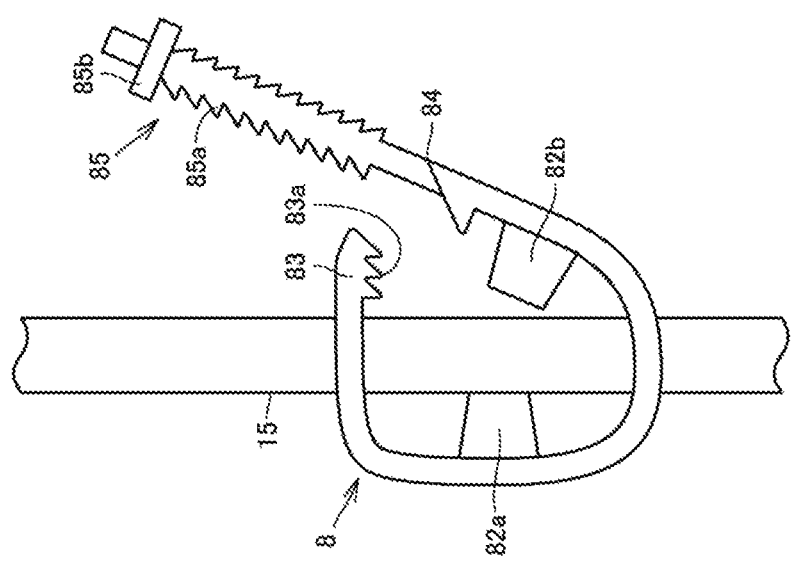

FIGS. 30A-30C are front views illustrating a usage state of the first configuration example of the embodiment. FIG. 30A illustrates a state in which the tube 15 is used for transfusion or the like. The first lock mechanism (the first sawtooth-shaped portion 83 and the claw 84) is released such that the tube 15 is not closed. As illustrated in FIG. 30B, when usage of the tube 15 is finished, the tube 15 is pressure-narrowed by the pressure portions 82a and 82b of the tube clamp 8 and the first lock mechanism locks the clamped state of the tube 15 in order to detach the tube 15 from the dropping rate controller or the like.

In the first configuration example of the embodiment, as further illustrated in FIG. 30C, the first lock mechanism is irreversibly locked by the second lock mechanism (the second sawtooth-shaped portion 85 and the lock member 85b).

To be specific, the lock member 85b is a plate-like member having a hole having a size adjusted so as to be moved downward only on the sawtooth-shaped portion. When the lock member 85b is once pushed down to a lower portion of the second sawtooth-shaped portion 85, it cannot be returned to the upper side with the second sawtooth-shaped projection 85a. As illustrated in FIG. 30C, when the lock member 85b is pushed down until it abuts against the first sawtooth-shaped portion 83, the lock member 85b cannot be moved upward and the clamped state of the tube 15 by the first lock mechanism can be thereby maintained reliably.

As described above, the tube clamp in the first configuration example of the embodiment can irreversibly lock the tube clamped state with the second lock mechanism.

(Application)

Next, an application of the first configuration example of the embodiment will be described with reference to FIGS. 31A-31C. The application is an example in which the tube clamp 8 in the first configuration example and the dropping rate controller 6 are combined.

The tube 15 is used in combination with the dropping rate controller 6. The dropping rate controller 6 includes a cover 61 for preventing the tube 15 from being detached. The cover 61 is normally locked so as not to be opened. The cover 61 is unlocked so as to be opened by causing the tip of the second sawtooth-shaped portion 85 of the tube clamp 8 to be pressed against a release button 61a provided above an insertion port 61b. When the cover 61 is opened, the tube can be detached from the dropping rate controller 6.

When a usage state of the tubes 15 and 16 (state in which the drip infusion is executed) illustrated in FIG. 31A is finished, the first lock mechanism of the tube clamp 8 is locked and a state illustrated in FIG. 31B is established. In the state illustrated in FIG. 31B, when the tubes 15 and 16 are pulled out upward, the second sawtooth-shaped portion 85 of the tube clamp 8 is pushed into the insertion port 61b and the tip of the second sawtooth-shaped portion 85 is pressed against the release button 61a (see FIG. 31C) and the cover 61 is unlocked.

In this case, (even when the second lock mechanism of the tube clamp 8 is not locked), the lock member 85b is pushed down by the cover 61 and the second lock mechanism is locked (see FIG. 31C). With this locking, when the tube is detached from the dropping rate controller 6, the tube clamp 8 (closed state of the tube 15) is necessarily locked irreversibly, thereby being capable of preventing flow-down (free flow) of the liquid in the tube reliably.

Thus, in this application, an operation of locking the second lock mechanism of the tube clamp 8 is necessarily required in order to perform an operation of detaching the tube from the dropping rate controller 6. Therefore, free flow can be prevented reliably.

The above-described application is not limited to the configuration as illustrated in FIGS. 31A-31C and can be applied to various configurations as long as the release button can be pushed only when the tube clamp 8 (second lock mechanism) is irreversibly locked. For example, the cover 61 may be opened by an effect of the characteristic shape of the tube clamp 8 in the state in which the second lock mechanism is locked. When the third configuration example, which will be described later, is employed, a key hole having a shape enabling insertion only when a slide plate is accommodated in a main body may be provided.

Second Configuration Example

A tube clamp in the second configuration example of the embodiment will be described with reference to FIG. 32 and FIG. 33. The tube clamp in the second configuration example is an improved product of a so-called clip-type (alligator-type) tube clamp.

As illustrated in FIG. 32, a tube clamp 91 in the second configuration example of the embodiment includes not only a first lock mechanism (a first claw 913 and a first claw receiving portion 913a) for clamping the tube 15, which is similar to the existing one, but also a second lock mechanism (a second claw 914 and a second claw receiving portion 915) for preventing the first lock mechanism from being released. The second lock mechanism is configured so as not to be released after being once locked, that is, configured to be capable of making irreversible locking.

Figure 33A:
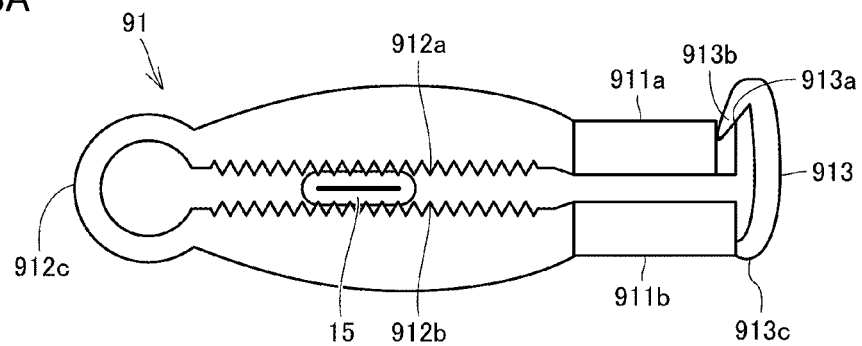
Figure 33A:
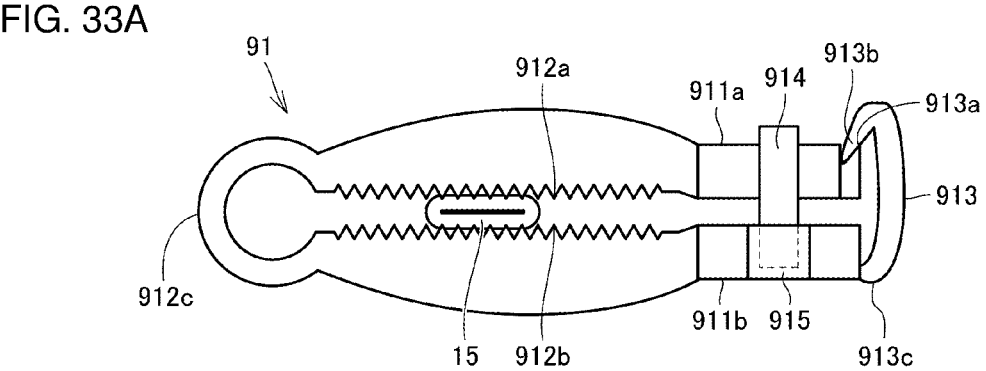

As illustrated in FIG. 33A, grip portions 911a and 911b of the tube clamp 91 are pressed from both of the sides to pinch the tube 15 by pressure portions (sawtooth-shaped projections) 912a and 912b. With this, the tube 15 can be clamped. A folded portion 913b of the first claw 913 is hooked on the first claw receiving portion 913a to cause the first lock mechanism to reversibly lock the tube clamp 91. However, locking by the first lock mechanism is reversible locking capable of being released by detaching the claw.

Figure 33C:
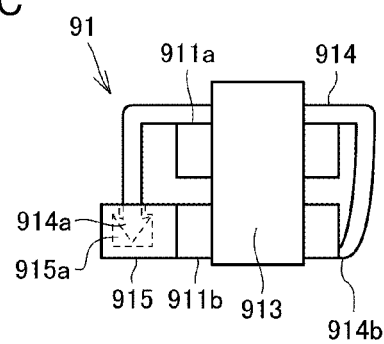
FIG. 33C is a front view illustrating the configuration in the second configuration example of the sixth embodiment.

Then, with reference to FIG. 33B, a barb portion 914a of the second claw 914 is pushed so as to be inserted into a perforated portion 915a of the second claw receiving portion 915. As illustrated in FIG. 33C, the perforated portion 915a has a shape of being one-size wider at the deep side than a cavity and the barb portion 914a is configured such that the once inserted second claw 914 is not pulled out. With this, the second lock mechanism irreversibly locks the tube clamp 91.

The whole tube clamp 91 is formed by a resin mold, for example, and has portions (a connecting portion 912c between the pressure portions 912a and 912b, a connecting portion 913c between the first claw 913 and the grip portion 911b, and a connecting portion 914b between the second claw 914 and the grip portion 911b) having plasticity with the thickness of the material, and other portions having rigidity.

Third Configuration Example

A tube clamp in the third configuration example of the embodiment will be described with reference to FIG. 34. The tube clamp in the third configuration example is an improved product of a so-called slide type tube clamp.

Figure 34:
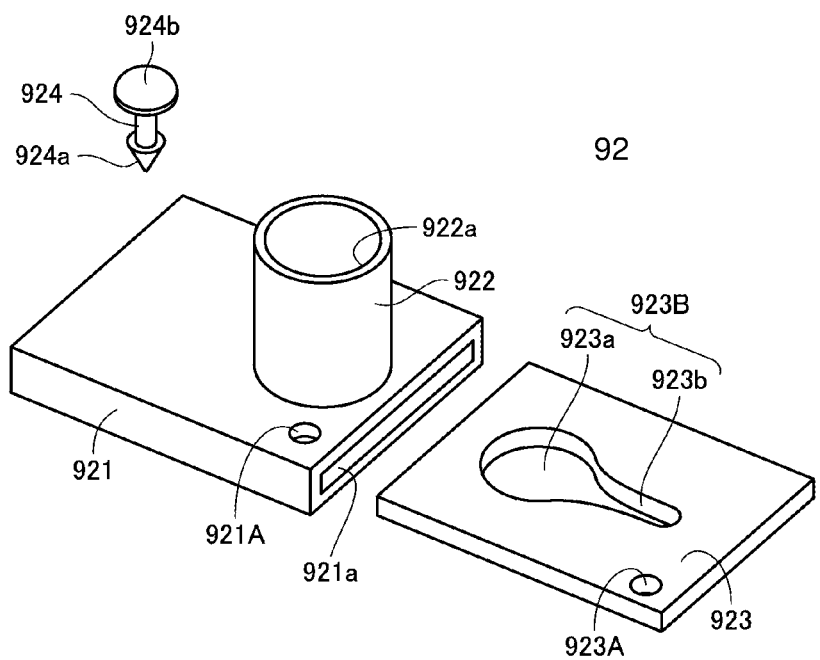
FIG. 34 is a perspective view illustrating the configuration in a third configuration example of the sixth embodiment.

As illustrated in FIG. 34, a tube clamp 92 in the third configuration example of the embodiment includes not only a first lock mechanism (a slide plate 923 and a main body plate 921) for clamping the tube 15 but also a second lock mechanism (a hole 923A of the slide plate 923, a hole 921A of the main body plate 921, and a lock pin 924) for preventing the first lock mechanism from being released. The second lock mechanism is configured so as not to be released after being once locked, that is, configured to be capable of making irreversible locking.

The tube clamp 92 in this configuration example includes the main body plate 921, the slide plate 923, and the lock pin 924.

The slide plate 923 has a through-hole 923B formed by an insertion portion 923a and a narrow portion 923b (throttle portion) and the hole 923A. The main body plate 921 includes a perforated portion 921a into which the slide plate 923 is inserted, a cylindrical portion 922 having an insertion hole 922a, and the hole 921A penetrating through both of the surfaces of the main body plate 921. The lock pin 924 has a barb portion 924a and a head portion 924b.

Figure 35:
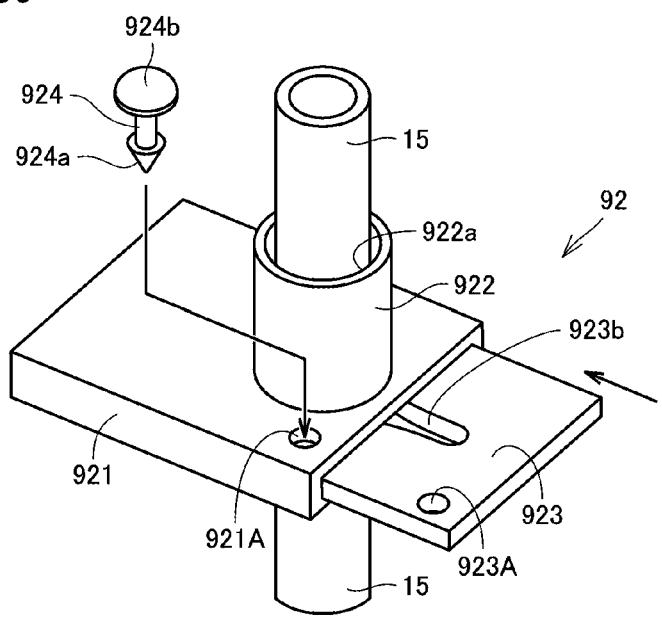
FIG. 35 is a perspective view for explaining a usage method of the third configuration example of the sixth embodiment.

Next, a usage method in the configuration example will described with reference to FIG. 35. First, as illustrated in FIG. 35, the slide plate 923 is inserted into the perforated portion 921a of the main body plate 921 to a position at which the insertion portion 923a and the insertion hole 922a are identical to each other. Then, the tube 15 is inserted through the insertion hole 922a.

After the tube 15 is completely inserted, the slide plate 923 is made to slide and is further pressed to the deep side of the perforated portion 921a, so that the tube 15 can be clamped by the narrow portion 923b.

The tube clamp 92 is locked in a state of clamping the tube 15 by inserting the lock pin 924 into the hole 921A and the hole 923A in this state. The barb portion 924a at the tip of the lock pin 924 is configured such that the lock pin 924 is not pulled out from the hole 921A and the hole 923A after once penetrating through them.

In the configuration example, all of the components can be formed by relatively hard members (hard resin or the like). Therefore, it is difficult to break the lock mechanism, thereby being capable of maintaining locking of the tube clamp more reliably.

It should be considered that the embodiments disclosed herein are exemplary in all points and are not limiting. The range of the present invention is indicated not by the above description but by the scope of the invention and is intended to encompass all changes within equivalent meanings and range to the scope of the invention.

REFERENCE SIGNS LIST

1 DROPPING RATE MEASURING DEVICE (LIQUID DROPLET VOLUME MEASURING DEVICE)
11 DRIP INFUSION CYLINDER
12 NOZZLE
13a (GROWING) LIQUID DROPLET
13b (DROPPING) LIQUID DROPLET
14 LIQUID POOL
15, 16 TUBE
21 CAMERA (IMAGING UNIT)
21a VISIBLE LIGHT CUT FILTER
22 ILLUMINATION DEVICE
22a INFRARED LED
22b DIFFUSION PLATE
3 ADJUSTING DEVICE
31 ACTUATOR
32 CONTROLLER
33 CLIP
4 DATA PROCESSOR
41, 42 CIRCLE
43 CONTOUR
51 LIGHT EMITTING PORTION
52 LIGHT RECEIVING PORTION
53 REFLECTION-TYPE PHOTOSENSOR
6 DROPPING RATE CONTROLLER
61 COVER
61a RELEASE BUTTON
61b INSERTION PORT
7 HOUSING
71 DOOR
8, 80, 91, 92 TUBE CLAMP
81a, 81b CAVITY
82a, 82b PRESSURE MEMBER
83 FIRST SAWTOOTH-SHAPED PORTION
83a SAWTOOTH-SHAPED PROJECTION
84 CLAW
85 SECOND SAWTOOTH-SHAPED PORTION

85a SAWTOOTH-SHAPED PROJECTION
85b LOCK MEMBER
911a, 911b GRIP PORTION
913c CONNECTING PORTION
912a, 912b PRESSURE PORTION
912c CONNECTING PORTION
913 FIRST CLAW
913a FIRST CLAW RECEIVING PORTION
913b FOLDED PORTION
914 SECOND CLAW
914a BARB PORTION
914b CONNECTING PORTION
915 SECOND CLAW RECEIVING PORTION
915a PERFORATED PORTION
921 MAIN BODY PLATE
921a PERFORATED PORTION
921A HOLE
922 CYLINDRICAL PORTION
922a INSERTION HOLE
923 SLIDE PLATE
923a INSERTION PORTION
923b NARROW PORTION
923A HOLE
923B THROUGH-HOLE
924 LOCK PIN
924a BARB PORTION

The invention claimed is:

1. A dropping rate measuring device for measuring a flow rate of liquid droplets which grow on a lower end of a nozzle and intermittently drop from the lower end of the nozzle, the device comprising:
a camera configured to image a liquid droplet growing on the lower end of the nozzle at a plurality of time points and acquire image data of the growing liquid droplet;
a processor configured to calculate the flow rate by analyzing the image data; and
a counter that detects the liquid droplets dropping from the lower end of the nozzle and counts the number of liquid droplets that have dropped from the lower end of the nozzle,
wherein the processor is further configured to calculate an estimated volume of a dropping liquid droplet after dropping from the lower end of the nozzle by analyzing the image data, and calculate the flow rate from the number of liquid droplets that have dropped and the estimated volume, and
wherein operation of the camera is stopped after the estimated volume of at least one dropping liquid droplet is calculated.

2. The dropping rate measuring device according to claim 1,
wherein the image data is a series of moving images imaged by the camera, and
the processor is further configured as the counter by detecting the liquid droplets dropping from the lower end of the nozzle by analyzing the image data, and counting the number of liquid droplets that have dropped from the lower end of the nozzle.

3. The dropping rate measuring device according to claim 1,
wherein the counter comprises:
a light emitter configured to emit light toward the liquid droplets; and
a light receiver configured to detect variation in a transmission amount of the light, shielding of the light, variation in a reflection amount of the light, or variation in refraction of the light by the growing liquid droplet or the dropping liquid droplet, and
the light receiver is further configured to detect liquid droplets dropping from the lower end of the nozzle.

4. The dropping rate measuring device according to claim 1,
wherein the processor is further configured to:
calculate the estimated volume of the dropping liquid droplet by fitting a circle to the growing liquid droplet in each piece of image data and calculating a radius of the circle or a center position of the circle.

5. The dropping rate measuring device according to claim 1,
wherein the processor is further configured to:
calculate a volume of the growing liquid droplet based on a contour of the growing liquid droplet in each piece of image data, and
calculate the estimated volume of the dropping liquid droplet based on the volume of the growing liquid droplet.

6. The dropping rate measuring device according to claim 1,
wherein the processor is further configured to calculate a volume increase speed of the growing liquid droplet by analyzing the image data, and set the volume increase speed as the flow rate.

7. The dropping rate measuring device according to claim 6,
wherein the processor is further configured to:
calculate the volume increase speed by fitting a circle to the growing liquid droplet in each piece of image data and calculating a variation amount of at least any one of a radius of the circle and a center position of the circle.

8. The dropping rate measuring device according to claim 6,
wherein the processor is further configured to:
calculate a volumes of the growing liquid droplet based on a contour of the growing liquid droplet in each piece of image data, and
calculate the volume increase speed based on the volume of the growing liquid droplet.

9. The dropping rate measuring device according to claim 1, further comprising an illumination device that illuminates the growing liquid droplet.

10. The dropping rate measuring device according to claim 9,
wherein the illumination device is a stroboscope configured to repeatedly emit light at a constant interval, or wherein illumination device emits light having a wave length, which is not visible.

11. The dropping rate measuring device according to claim 1,
wherein the camera includes an optical filter configured to filter out at least a partial range of visible light.

12. The dropping rate measuring device according to claim 1,
wherein dynamic portions of the image data are extracted by comparing each piece of image data and removing pieces with no variations.

13. A dropping rate controller comprising:
the dropping rate measuring device according to claim 1; and
an adjusting device for adjusting the flow rate based on the flow rate of the liquid droplets measured by the dropping rate measuring device.

14. The dropping rate measuring device according to claim 1,
wherein operation of the counter is stopped before the operation of the camera is stopped and the counter is operated after the operation of the camera is stopped.

15. The dropping rate measuring device according to claim 1,
wherein the operation of the camera is stopped after estimated volumes of a plurality of dropping liquid droplets are calculated and an average value of the estimated volumes is calculated, and
the flow rate is calculated from the number liquid droplets that have dropped and the average value of the estimated volumes.

16. A drip infusion device comprising:
the dropping ping rate controller according to claim 13;
a drip infusion cylinder;
the nozzle from which liquid droplets intermittently drop into the drip infusion cylinder; and
a tube for discharging the liquid droplets that have dropped into the drip infusion cylinder from the drip infusion cylinder.

17. The drip infusion device according to claim 16,
wherein the drip infusion cylinder is transparent,
the tube is flexible,
the adjusting device comprises an actuator and is configured to adjust the flow rate by pressing a part of the flexible tube from an outside by the actuator to adjust an opening of a flow path in the flexible tube.

18. The drip infusion device according to claim 17,
wherein an inner wall of the drip infusion cylinder is hydrophilic.

* * * * *

UNITED STATES PATENT AND TRADEMARK OFFICE
CERTIFICATE OF CORRECTION

PATENT NO. : 10,300,197 B2
APPLICATION NO. : 15/647733
DATED : May 28, 2019
INVENTOR(S) : Atsuhiko Hirata et al.

It is certified that error appears in the above-identified patent and that said Letters Patent is hereby corrected as shown below:

In the Specification

Column 17, Line 10, "receiving portion" should read --receiving portion 52--

In the Claims

Column 28, Line 51 (Claim 10), "wherein illumination" should read --wherein the illumination--

Signed and Sealed this
Fifteenth Day of September, 2020

Andrei Iancu
*Director of the United States Patent and Trademark Office*